United States Patent
Katsuura et al.

(10) Patent No.: US 7,619,120 B2
(45) Date of Patent: *Nov. 17, 2009

(54) PROCESSES FOR THE PREPARATION OF DIPHENYLSULFONE COMPOUNDS

(75) Inventors: Kiyoshi Katsuura, Takaoka (JP); Tomoya Hidaka, Ichihara (JP); Yutaka Takashina, Takahagi (JP); Yasuo Ohnuki, Kitaibaraki (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/950,889

(22) Filed: Sep. 27, 2004

(65) Prior Publication Data

US 2005/0065377 A1  Mar. 24, 2005

Related U.S. Application Data

(62) Division of application No. 10/239,483, filed as application No. PCT/JP02/00410 on Jan. 22, 2002, now Pat. No. 6,831,201.

(30) Foreign Application Priority Data

Jan. 22, 2001  (JP) ............................... 2001-13638
Mar. 23, 2001  (JP) ............................... 2001-84218
Apr. 5, 2001  (JP) ............................... 2001-107548

(51) Int. Cl.
  *C07C 315/06* (2006.01)
(52) U.S. Cl. .................................................. 568/33
(58) Field of Classification Search .................. 568/28, 568/32, 33, 34, 716, 731, 744, 745, 749, 568/750, 759, 810
See application file for complete search history.

(56) References Cited

U.S. PATENT DOCUMENTS

| | | | |
|---|---|---|---|
| 3,065,274 A | 11/1962 | Vegter et al. | |
| 3,408,402 A | 10/1968 | Callighan et al. | |
| 3,784,518 A | 1/1974 | Paulik | |
| 4,446,209 A | 5/1984 | Iwakura et al. | |
| 4,568,766 A | 2/1986 | Yahagi et al. | |
| 4,616,239 A | 10/1986 | Yahagi et al. | |
| 5,284,978 A * | 2/1994 | Kinishi et al. | 568/33 |
| 5,414,149 A | 5/1995 | Garrett et al. | |
| 5,463,133 A | 10/1995 | Sato et al. | |
| 6,509,126 B1 | 1/2003 | Whitesides et al. | |
| 6,590,126 B1 | 7/2003 | Sanpei et al. | |

FOREIGN PATENT DOCUMENTS

| | | |
|---|---|---|
| JP | 58-20493 | 5/1983 |
| JP | 58164131 | 9/1983 |
| JP | 60-56949 A | 2/1985 |
| JP | 3-258760 A | 11/1991 |
| JP | 04000715 | 1/1992 |
| JP | 5-255234 | 5/1993 |
| JP | 05117224 | 5/1993 |
| JP | 05186417 | 7/1993 |
| JP | 6-25148 | 1/1994 |
| JP | 10114735 | 5/1998 |
| JP | 10-158235 | 6/1998 |
| JP | 11-124362 | 5/1999 |
| JP | 2001-011001 | 1/2001 |

OTHER PUBLICATIONS

Chemical Engineer's Handbook, Perry, ed. (1963) p. 13-2.*
Chemical Engineer's Handbook, Perry ed., 5th ed. pp. 16-2-16-4 and 19-4-19-6.*
Extraction' in Ullmann's Encyclopedia of Industrial Chemistry, Copyright © 2008 by John Wiley & Sons, pp. 1-60.*
Joseph, et al, 1995. "Direct Conversion of Alcohols into the Corresponding Iodides". Tetrahedron Letters 36(4): 609-612.

* cited by examiner

*Primary Examiner*—Karl J Puttlitz
(74) *Attorney, Agent, or Firm*—Darby & Darby P.C.

(57) ABSTRACT

The present invention is to provide methods for producing highly pure 4,4'-dihydroxydiphenyl sulfone monoethers advantageously in industrial production.

In a process for producing a compound represented by Formula (I)

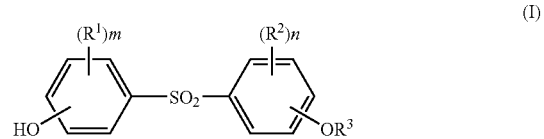

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), (1) a pH adjustment is carried out twice or more in the purification process, (2) an excessive amount of alkyl halide used is removed, (3) a solvent, such as water, containing 0.05 ppm or less of iron components is used, (4) tanks with corrosion-resistant layers over the inner walls are used, (6) a chelating agent is added, and (7) a means of drying with mechanical stir is applied.

44 Claims, No Drawings ns filed Sep. 20, 2002, now U.S. Pat. No. 6,831,201 which is a 35 USC 371 national stage application of PCT/JP02/00410 with an international file date of Jan. 22, 2002.

PROCESSES FOR THE PREPARATION OF DIPHENYLSULFONE COMPOUNDS

RELATED APPLICATIONS

This application is a divisional of U.S. patent application Ser. 10/239,483 filed Sep. 20, 2002, now U.S. Pat. No. 6,831,201 which is a 35 USC 371 national stage application of PCT/JP02/00410 with an international file date of Jan. 22, 2002.

TECHNICAL FIELDS

The present invention relates to processes for the preparation of 4,4'-dihydroxydiphenyl sulfone monoethers useful as developers for thermal recording agents.

BACKGROUND ART

Dihydroxydiphenyl sulfone monoethers are developers excellent in coloring sensitivity, preservability, heat resistance and other properties, and are often used for thermal recording papers for facsimiles, barcodes, receipts and the like.

Processes for the preparation of, for example, a 4-alkoxy-4'-hydroxydiphenyl sulfone (which may hereinafter refer to as the target compound), among the dihydroxydiphenyl sulfone monoethers, by a reaction of 4,4'-dihydroxydiphenyl sulfone (which may hereinafter refer to as BPS) with a halogen compound such as an alkyl halide in the presence of an alkali in a polar solvent such as dimethylformamide, dimethyl sulfoxide and alcohol, have been disclosed in each of Japanese Patents Laid-open Nos. Sho 58-20493, Sho 58-82788, Sho 60-13852, Sho 60-56949 and Hei 6-25148. These methods have a drawback that it is difficult to improve reaction selectivity because of use of solvents dissolving reaction reagents and reaction products very well. A problem has been a production of a noticeable amount of a diether derivative byproduct, 4,4'-dihydroxydiphenyl sulfone diether.

WO 91/11433 has disclosed that a reaction of BPS with an alkyl halide in the presence of 1.5 to 3 moles of an alkali to a mole of BPS in 0.3 to 1.5 parts by weight of an aqueous solvent to a part by weight of 4,4'-dihydroxydiphenyl sulfone gives satisfactory results in both selectivity and yield.

Japanese Patent Laid-open No. Hei 3-258760 describes a method for separating BPS from a 4-alkoxy-4'-hydroxydiphenyl sulfone, in which an aqueous alkali solution and alcohols or ketones that do not mix with water are added to mix with a mixture containing BPS and a 4-alkoxy-4'-hydroxydiphenyl sulfone, and the 4-alkoxy-4'-hydroxydiphenyl sulfone is moved into the organic layer and the alkali metal salt of BPS into the aqueous layer for separation.

In Japanese Patent Laid-open No. Hei 60-56949, a purification method of a 4-alkoxy-4'-hydroxydiphenyl sulfone is described in which a solution of a water-nonmiscible organic solvent containing a 4-alkoxy-4'-hydroxydiphenyl sulfone and unreacted BPS that is produced when BPS is alkylated or by other methods is shaken with an aqueous solution of hydrogen carbonate so that BPS moves into water for removal.

Japanese Patent Laid-open No. Hei 5-255234 describes a method for producing a 4-alkoxy-4'-hydroxydiphenyl sulfone, in which an alkyl halide is added to a two-phase solvent system consisting of an aqueous solution of an alkaline compound in which BPS is dissolved and a water-nonmiscible organic solvent, and an alkaline compound is added to keep pH to 7.5 to 9.5, in a method for producing a 4-alkoxy-4'-hydroxydiphenyl sulfone by reacting BPS with an alkyl halide.

Japanese Patent Laid-open No. Hei 10-158235 has disclosed a method for purifying a 4-alkoxy-4'-hydroxydiphenyl sulfone, in which an alkali metal ion donor is added to an aqueous solution of a mixture containing a BPS alkali metal salt and an alkali metal salt of a 4-alkoxy-4'-hydroxydiphenyl sulfone to deposit and separate the alkali metal salt of 4-alkoxy-4'-hydroxydiphenyl sulfone, followed by treatment of the salt with an acid.

In the above production methods, the reaction solution contains the target compound as well as unreacted BPS, a byproduct of 4,4'-dialkoxydiphenyl sulfone and other impurities, as a side reaction proceeds simultaneously. These impurities damage the performance of the product when used as a developer. Therefore, a purification process to remove the impurities from the reaction solution is required.

Of the said impurities, the 4,4'-dialkoxydiphenyl sulfone, which is insoluble in water, can be removed in a way that the reaction solution is made an aqueous alkaline solution, a water-nonmiscible organic solvent is added and the sulfone is extracted into the organic layer for separation.

To remove unreacted BPS, a water-nonmiscible organic solvent is added to the reaction solution to produce a two-phase system consisting of an organic and an aqueous layers, the pH value of the aqueous layer is adjusted to a preset value to move the target compound into the organic layer and BPS into the aqueous layer, then the organic layer is separated, washed with water if necessary and cooled, and deposited crystals are separated by filtration so as to give the target compound. This separation/purification method utilizes the difference in acidity between the phenolic hydroxyl groups of BPS and the target compound.

DISCLOSURE OF THE INVENTION

However, the difference in acidity between the phenolic hydroxyl groups of BPS and the target compound is subtle. BPS is completely removed if the pH of the aqueous layer is higher than the preset value. Then, it becomes difficult to separate the target compound completely into the organic layer, resulting in a large loss of the target compound. On the contrary, if the pH of the aqueous layer is lower than the preset value, the loss of the target compound is small. There has been a problem however that BPS moves into the organic layer so as to mix into the target compound as an impurity.

As described above, 4,4'-dihydroxydiphenyl sulfone monoethers produced by methods of the prior art may not have been satisfactory in terms of purity. Particularly when a reaction solution obtained from a reaction of materials at high concentrations is purified according to the aforementioned methods, BPS often tends to mix into the target compound as an impurity because of insufficient purification.

4,4-Dihydroxydiphenyl sulfone monoethers are mainly used as developers. There have however been problems that, for example, a so-called background foggy phenomenon, which is the coloring of the surrounding area of a heated part on a thermal recording paper, occurs if 0.4% or more of BPS is contained in 4,4'-dihydroxydiphenyl sulfone monoethers. Therefore, development of production methods for isolating highly pure 4,4'-dihydroxydiphenyl sulfone monoethers has been looked for.

When 4,4'-dihydroxydiphenyl sulfone monoethers are produced in industrial scales, reaction solutions may sometimes be colored. In this case, the products, 4,4'-dihydroxydiphenyl sulfone monoethers, are also colored. It is sometimes difficult to decolor the products (to remove coloring substances) completely, even if processes such as decoloring and purification using activated carbon and the like are carried out afterward. Another problem has been a requirement of a new process for removing the added decoloring agents.

As described above, 4,4'-dihydroxydiphenyl sulfone monoethers are mainly used as developers. Because of the purpose of their use, developers are not satisfactory even if slightly colored.

It has been required therefore to establish industrial processes for producing non-colored, highly pure 4,4'-dihydroxydiphenyl sulfone monoethers in high yield.

In addition, when 4,4'-dihydroxydiphenyl sulfone monoethers are taken out as crystals at the final stage and the crystals are dried by a hot dryer, the crystals may become lumps so that solvents cannot be removed completely. The monoethers containing solvents have a problem of performance as products. As 4,4'-dihydroxydiphenyl sulfone monoethers are used in the state of dispersing in solvents such as water, products of small crystal size, which are easily dispersed, are demanded. If there are block particles after the crystals are dried, a further process for pulverizing is required. To produce a product of small particle size, pulverization process work has sometimes become too complicated.

The present invention has been carried out in consideration of the aforementioned situations. It is an object of the present invention to provide methods for producing non-colored, highly pure 4,4'-dihydroxydiphenyl sulfone monoethers in high yield and advantageously in industrial production.

The inventors of the present invention have studied in earnest to solve the above problems. As a result, it has been found that the problems can be solved by that (1) BPS is removed efficiently if pH is adjusted step by step, (2) an alkyl halide used in the reaction remains and decomposes in the forming process so as to color the product, (3) the presence of metal ions, such as iron, in a solvent used in the production process causes coloring and substances producing the ions are removed, and (4) the product is dried with mechanical stir. Thus the present invention has been completed.

The present invention relates to (Composition 1) a process for the preparation of a compound represented by Formula (I)

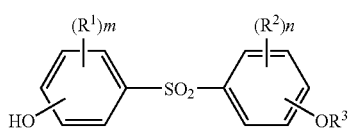

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), in which there are processes that an aqueous solution containing a compound of Formula (I) is adjusted pH to a preset value (P1), extracted with an organic solvent and separated to an organic and an aqueous layers, and that water or water adjusted to a fixed pH value is added to the separated organic layer in order to adjust the pH of the aqueous layer to a preset value (P2) for the separation of the organic layer;

(Composition 2) a process for the preparation of a compound of Formula (I) according to (Composition 1) in which the process that an aqueous solution containing a compound of Formula (I) is adjusted pH to a preset value (P1), extracted with an organic solvent and separated to an organic and an aqueous layers is a process that the aqueous layer of a two-phase solution consisting of water and a water-non-miscible organic solvent with a mixture containing a compound of Formula (I) is adjusted pH to the preset value (P1) for separating the organic layer;

(Composition 3) a process for the preparation of a compound of Formula (I) according to (Composition 1) or (Composition 2) in which the said P2 is set to a value different from the said P1;

(Composition 4) a process for the preparation of a compound of Formula (I) according to one of (Composition 1) to (Composition 3) in which the said P2 is set to a value lower than the said P1;

(Composition 5) a process for the preparation of a compound of Formula (I) according to one of (Composition 1) to (Composition 4) in which the said P1 is set in a range of 8.4 and 8.7 and the said P2 between 8.3 and 8.6;

(Composition 6) a process for the preparation of a compound of Formula (I) according to one of (Composition 1) to (Composition 5) in which the aqueous solution containing a compound of Formula (I) is an aqueous solution containing the reaction product obtained from a reaction of a compound represented by Formula (II)

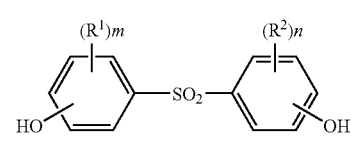

(wherein, $R^1$ and $R^2$ are each independently halogen, alkyl having 1 to 8 carbons or alkenyl having 2 to 8 carbons; m and n are each independently 0 or an integer of 1 and 4) with a compound of Formula (III)

(wherein, $R^3$ is alkyl having 1 to 8 carbons, alkenyl having 2 to 8 carbons, cycloalkyl having 3 to 8 carbons or optionally substituted aralkyl, and X is halogen) in a solvent in the presence of a base;

(Composition 7) a process for the preparation of a compound of Formula (I)

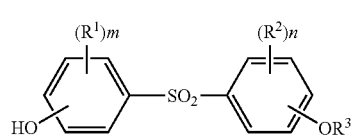

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), characterized in that, in a method for producing a compound of Formula (I) by reacting a compound of Formula (II)

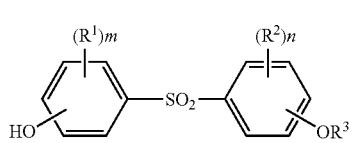

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), characterized in that, in a method for producing a compound of Formula (I) by reacting a compound of Formula (II)

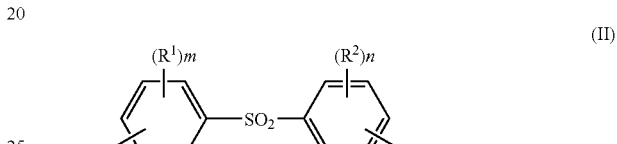

(wherein, $R^1$, $R^2$, m and n are as defined above) with a compound of Formula (III)

$$R^3-X \qquad (III)$$

(wherein $R^3$ is as defined above and X is halogen) in a solvent in the presence of a base and the obtained reaction solution is purified, the compound of Formula (III) in the organic solvent is 5% by weight or less in concentration in the process for purifying the reaction mixture of the compounds of Formulae (II) and (III) with water and an organic solvent;

(Composition 16) a process for the preparation of a compound of Formula (I) according to (Composition 15) in which the compound of Formula (III) in the organic solvent is 2% by weight or less in concentration;

(Composition 17) a process for the preparation of a compound of Formula (I) according to (Composition 15) in which the compound of Formula (III) in the organic solvent is 1% by weight or less in concentration;

(Composition 18) a process for the preparation of a compound of Formula (I)

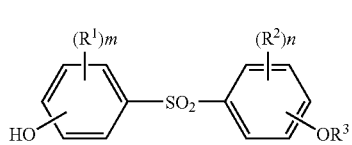

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), characterized in that, in a method for producing a compound of Formula (I) with a process for reacting a compound of Formula (II)

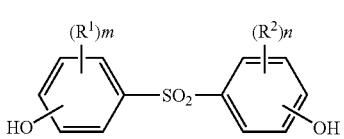

(wherein, $R^1$, $R^2$, m and n are as defined above) with a compound of Formula (III)

$$R^3-X \qquad (III)$$

(wherein $R^3$ is as defined above and X is halogen) in a solvent in the presence of a base and the obtained reaction solution is purified, a process is provided that the compound of Formula (III) is removed from the solution produced by the reaction of the compounds of Formulae (II) and (III);

(Composition 8) a process for the preparation of a compound of Formula (I) according to (Composition 7) in which the said reaction solution is the reaction solution after the reaction of compounds of Formulae (II) and (III) is finished;

(Composition 9) a process for the preparation of a compound of Formula (I) according to (Composition 7) or (Composition 8) in which the process for removing the compound of Formula (III) from the reaction solution is provided immediately after the compounds of Formulae (II) and (III) are reacted in a solvent in the presence of an alkali;

(Composition 10) a process for the preparation of a compound of Formula (I) according to one of (Composition 7) to (Composition 9) in which a process for adjusting pH of solutions including the reaction solution is provided in the production method of a compound of Formula (I), and the process for removing the compound of Formula (III) from the reaction solution is provided immediately before the process for adjusting the pH of the solutions including the reaction solution;

(Composition 11) a process for the preparation of a compound of Formula (I) according to one of (Composition 7) to (Composition 10) in which the process for removing the compound of Formula (II) is a process for removing the compound of Formula (E) together with the reaction solvent from the reaction solution by distillation;

(Composition 12) a process for the preparation of a compound of Formula (I) according to one of (Composition 7) to (Composition 10) in which the process for removing the compound of Formula (III) is a process for removing the compound together with a mixture of water and a solvent azeotropic with water by distillation;

(Composition 13) a process for the preparation of a compound of Formula (I) according to one of (Composition 7) to (Composition 12) in which the reaction solvent is water;

(Composition 14) a process for the preparation of a compound of Formula (I) according to one of (Composition 7) to (Composition 13) in which a process for depositing the compound of Formula (I) from an organic solvent as crystals is provided in the production method of the compound of Formula (I), and the compound of Formula (III) is removed so that the concentration of the compound in the organic solvent is 1% by weight or less;

(Composition 15) a process for the preparation of a compound of Formula (I)

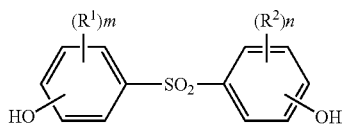 (II)

(wherein, $R^1$, $R^2$, m and n are as defined above) with a compound of Formula (III)

 (III)

(wherein $R^3$ is as defined above and X is halogen) in the presence of 1.5 to 3 moles of an alkali to a mole of the compound of Formula (II) in 0.3 to 1.5 parts by weight of an aqueous solvent to a part by weight of the compound of Formula (II) and the compound of Formula (III) is removed by distillation, the compound of Formula (III) is heated to distill out and then water is further added to distill the compound of Formula (III) to remove;

(Composition 19) a process for the preparation of a compound of Formula (I) according to (Composition 18) in which an amount of water added is in the range of 0.03 and 0.1 parts by weight to a part by weight of the compound of Formula (II);

(Composition 20) a process for the preparation of a compound of Formula (I) according to (Composition 18) in which an amount of water added is in the range of 0.04 and 0.08 parts by weight to a part by weight of the compound of Formula (II);

(Composition 21) a process for the preparation of a compound of Formula (I) according to (Composition 18) in which water is added separately over two or more times;

(Composition 22) a process for the preparation of a compound of Formula (I) according to (Composition 21) in which an amount of water added at the beginning is in the range of 0.03 and 0.1 parts by weight to a part by weight of the compound of Formula (II);

(Composition 23) a process for the preparation of a compound of Formula (I) according to (Composition 21) in which an amount of water added is between 0.04 and 0.08 parts by weight to a part by weight of the compound of Formula (II);

(Composition 24) a process for the preparation of a compound of Formula (I)

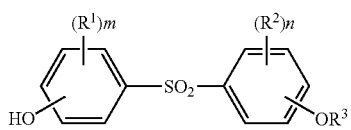 (I)

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), characterized in that, in a method for producing a compound of Formula (I) that a reaction is carried out in a solvent to give the compound of Formula (I), a solvent containing 0.05 ppm or less of iron components is used as the solvent;

(Composition 25) a process for the preparation of a compound of Formula (I) according to (Composition 24) in which the reaction solvent is a reaction solvent containing water;

(Composition 26) a process for the preparation of a compound of Formula (I)

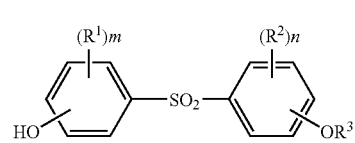 (I)

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), in which water containing 0.05 ppm or less of iron components is used as the water in the purification process for removing compounds, other than the compound of Formula (I), from the mixture containing the compound of Formula (I);

(Composition 27) a process for the preparation of a compound of Formula (I)

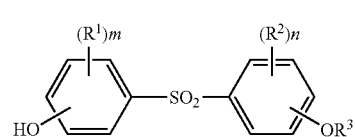 (I)

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), in which a tank with a corrosion-resistant layer over the inner wall is used in the reaction process for producing the compound of Formula (I);

(Composition 28) a process for the preparation of a compound of Formula (I)

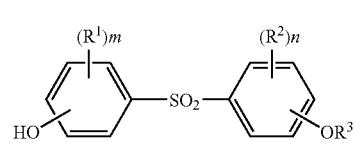 (I)

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), in which a tank with a corrosion-resistant layer over the inner wall is used in the purification process for removing compounds, other than the compound of Formula (I), from a mixture containing the compound of Formula (I);

(Composition 29) a process for the preparation of a compound of Formula (I) according to (Composition 24) or (Composition 25) in which the corrosion-resistant layer is a layer composed of at least one material selected from the group consisting of titanium, glasses and fluorine resins;

(Composition 30) a process for the preparation of a compound of Formula (I) according to one of (Composition 24) to (Composition 29) in which the reaction process for producing the compound of Formula (I) is a process for reacting a compound represented by Formula (II)

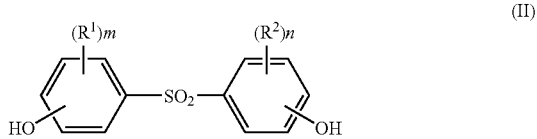

(wherein, $R^1$ and $R^2$ are each independently halogen, alkyl having 1 to 8 carbons or alkenyl having 2 to 8 carbons; m and n are each independently 0 or an integer of 1 and 4) with a compound of Formula (III)

(wherein, $R^3$ is as defined above and X is halogen) in a solvent in the presence of a base;

(Composition 31) a process for the preparation of a compound of Formula (I)

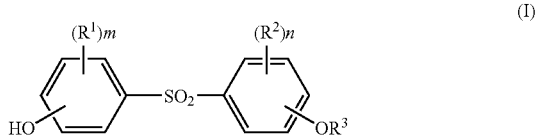

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), in which a chelating agent is added in the purification process for removing compounds, other than the compound of Formula (I), from a mixture containing the compound of Formula (I);

(Composition 32) a process for the preparation of a compound of Formula (I)

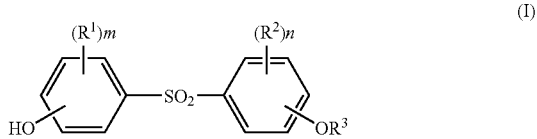

(wherein, $R^1$ and $R^2$ are each independently halogen, alkyl having 1 to 8 carbons or alkenyl having 2 to 8 carbons; m and n are each independently 0 or an integer of 1 to 4; and $R^3$ is alkyl having 1 to 8 carbons, alkenyl having 2 to 8 carbons, cycloalkyl having 3 to 8 carbons or optionally substituted aralkyl), characterized in that, in a method for producing the compound of Formula (I) with a drying process, the product is dried with mechanical stir in the drying process;

(Composition 33) a process for the preparation of a compound of Formula (I) according to (Composition 32) in which the product is heated to dry under reduced pressure with mechanical stir;

(Composition 34) a process for the preparation of a compound of Formula (I) according to (Composition 32) or (Composition 33) in which the compound of Formula (I) before drying is in the condition with a property of melting at a temperature below the melting point of the compound of Formula (I);

(Composition 35) a process for the preparation of a compound of Formula (I) according to one of (Composition 32) to (Composition 34) in which the compound of Formula (I) before drying is in the condition of forming a molecular compound with a solvent;

(Composition 36) a process for the preparation of a compound of Formula (I) according to (Composition 35) in which the solvent is an organic solvent;

(Composition 37) a process for the preparation of a compound of Formula (I) according to (Composition 36) in which the organic solvent is an aromatic hydrocarbon; and (Composition 38) a process for the preparation of a compound of Formula (I) according to one of claims 1 to 37 in which the compound of Formula (I) is a compound represented by Formula (IV)

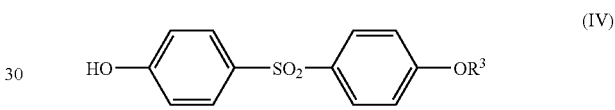

(wherein, $R^3$ is alkyl having 1 to 8 carbons, alkenyl having 2 to 8 carbons, cycloalkyl having 3 to 8 carbons or optionally substituted aralkyl).

The present invention is described in more detail in the following.

The present invention consists mainly of (Composition 1), (Composition 7), (Composition 15), (Composition 18), (Composition 24), (Composition 26), (Composition 27), (Composition 28), (Composition 31) and (Composition 32). Each of them relates to a method for producing a compound of Formula (I).

In Formula (I), $R^1$ and $R^2$ are each independently halogen such as fluorine, chlorine, bromine or iodine; alkyl having 1 to 8 carbons such as methyl, ethyl, n-propyl, isopropyl, n-butyl or t-butyl; or alkenyl having 2 to 8 carbons such as propenyl, isopropenyl or butenyl. m and n are each independently 0 or an integer of 1 to 4. When m and n are 1 or larger, substitution positions are not restricted.

In Formula (I), $R^3$ is alkyl having 1 to 8 carbons such as methyl, ethyl, n-propyl, isopropyl, n-butyl or t-butyl; alkenyl having 2 to 8 carbons such as propenyl, isopropenyl or butenyl; cycloalkyl having 3 to 8 carbons such as cyclopropyl, cyclopentyl or cyclohexyl; or optionally substituted aralkyl such as benzyl, 4-chlorobenzyl or 2-phenylethyl. Of them, a preferred compound of Formula (I) is a compound where R is alkyl having 2 to 4 carbons such as ethyl, n-propyl, isopropyl, n-butyl or t-butyl, or optionally substituted aralkyl such as benzyl. A compound where $R^3$ is isopropyl is particularly preferred. There are no particular restrictions on substitution positions of the hydroxyl group (OH group) and $OR^3$ group. It is however preferable that each of them is at the para position (4 or 4' position) to the sulfonyl group. The compound can be used favorably to produce a compound of Formula (IV) where each of the groups is at the 4 or 4' position.

Actual examples of compounds represented by Formula (IV) include 4-methoxy-4'-hydroxydiphenyl sulfone, 4-ethoxy-4'-hydroxydiphenyl sulfone, 4-n-propoxy-4'-hydroxydiphenyl sulfone, 4-isopropoxy-4'-hydroxydiphenyl sulfone, 4-n-butoxy-4'-hydroxydiphenyl sulfone, 4-sec-butoxy-4-hydroxydiphenyl sulfone and 4-t-butoxy-4'-hydroxydiphenyl sulfone. Of them, 4-isopropoxy-4'-hydroxydiphenyl sulfone is particularly preferred.

The production methods of the present invention can be applied not only to compounds of Formula (I) but also to compounds represented by Formula (V)

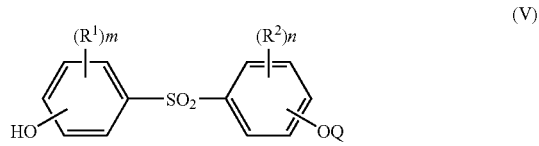

(wherein, $R^1$, $R^2$, m and n are as defined above, and Q is a group represented by Formula (VI)

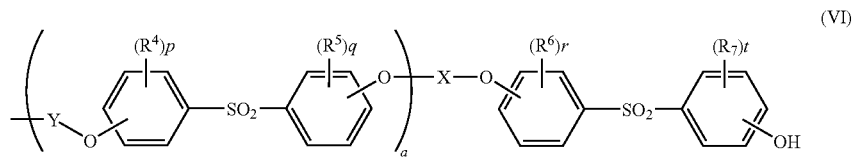

(wherein, X and Y are each independently a saturated or unsaturated, optionally substituted hydrocarbon having 1 to 12 carbons, saturated or unsaturated hydrocarbon having 1 to 12 carbons and ether bonds, a group represented by Formula (VII)

(wherein, $R^8$ is methylene or ethylene), or a group represented by Formula (VIII)

(wherein, $R^9$ is hydrogen or alkyl having 1 to 4 carbons); $R^4$ to $R^7$ are each independently halogen, alkyl having 1 to 8 carbons or alkenyl having 2 to 8 carbons; p, q, r and t are each independently 0 or an integer of 1 to 4; and a is 0 or an integer of 1 to 10). Particularly production methods relating to (Composition 11), (Composition 13) and (Composition 16) are preferably applied.

Actual examples of X and Y in Formula (VI) are each independently optionally substituted, saturated hydrocarbons having 1 to 12 carbons such as methylene, ethylene, trimethylene, tetramethylene, pentamethylene, hexamethylene, heptamethylene, octamethylene, nonamethylene, decamethylene, undecamethylene, dodecamethylene, methylmethylene, dimethylmethylene, methylethylene, methylene ethylene, ethylethylene, 1,2-dimethylethylene, 1-methyltrimethylene, 1-methyltetramethylene, 1,3-dimethyltrimethylene, 1-ethyl-4-methyl-tetramethylene, 2-hydroxytrimethylene, 2-hydroxy-2-methyltrimethylene, 2-hydroxy-2-ethyltrimethylene, 2-hydroxy-2-propyltrimethylene, 2-hydroxy-2-isopropyltrimethylene and 2-hydroxy-2-butyltrimethylene; optionally substituted, unsaturated hydrocarbons having 1 to 12 carbons such as vinylene, propenylene, 2-butenylene, ethynylene, 2-butynylene and 1-vinyl ethylene; and saturated or unsaturated hydrocarbons having 1 to 12 carbons and ether bonds such as ethylene oxyethylene, tetramethylene oxytetramethylene, ethylene oxyethylene oxyethylene, ethylene oxymethylene oxyethylene, and 1,3-dioxan-5,5-bismethylene.

Actual examples of $R^8$ in Formula (VII) include methylene and ethylene, and those of $R^9$ in Formula (VIII) include hydrogen and alkyl having 1 to 4 carbons such as methyl, ethyl, n-propyl, isopropyl, n-butyl and t-butyl.

Actual examples of $R^4$ to $R^7$ are each independently halogen such as fluorine, chlorine and bromine; alkyl having 1 to 8 carbons such as methyl, ethyl, n-propyl, isopropyl, n-butyl and t-butyl; and alkenyl having 2 to 8 carbons such as vinyl, propenyl, isopropenyl and butenyl.

The following are actual examples of compounds of Formula (V):
1) Compounds where X and/or Y in the formula are optionally substituted, saturated hydrocarbons having 1 to 12 carbons;

4-[4-(4-hydroxyphenylsulfonyl)phenoxy-4-butyloxy]-4'-[4-(4-hydroxyphenylsulfonyl)phenoxy-3-propyloxy]diphenyl sulfone, 4,4'-bis[4-(4-hydroxyphenylsulfonyl)phenoxy-2-ethyloxy]diphenyl sulfone, 4,4'-bis[4-(4-hydroxyphenylsulfonyl)phenoxy-3-propyloxy]diphenyl sulfone, 4,4'-bis[4-(4-hydroxyphenylsulfonyl)phenoxy-4-butyloxy]diphenyl sulfone, 4,4'-bis[4-(4-hydroxyphenylsulfonyl)phenoxy-5-pentyloxy]diphenyl sulfone, 4,4'-bis[4-(4-hydroxyphenylsulfonyl)phenoxy-6-hexyloxy]diphenyl sulfone, 4-[4-(4-hydroxyphenylsulfonyl)phenoxy-4-butyloxy]-4'-[4-(4-hydroxyphenylsulfonyl)phenoxy-2-ethyloxy]diphenyl sulfone, 4-[4-(4-hydroxyphenylsulfonyl)phenoxy-3-propyloxy]-4'-[4-(4-hydroxyphenylsulfonyl)phenoxy-2-ethyloxy]diphenyl sulfone, 4,4'-bis[4-[4-(2-hydroxyphenylsulfonyl)phenoxy]butyloxy]diphenyl sulfone, 4,4'-bis[4-[2-(4-hydroxyphenylsulfonyl)phenoxy]butyloxy]diphenyl sulfone, 1,1-bis[4-(4-hydroxyphenylsulfonyl)phenoxy]methane, 1,2-bis[4-(4-hydroxyphenylsulfonyl)phenoxy]ethane, 1,3-bis[4-(4-hydroxyphenylsulfonyl)phenoxy]propane, 1,4-bis[4-(4-hydroxyphenylsulfonyl)phenoxy]butane, 1,5-bis[4-(4-hydroxyphenylsulfonyl)phenoxy]pentane and 1,6-bis[4-(4-hydroxyphenylsulfonyl)phenoxy]hexane.

2) Compounds where X and/or Y in the formula are optionally substituted, unsaturated hydrocarbons having 1 to 12 carbons;

1,2-bis[4-(4-hydroxyphenylsulfonyl)phenoxy]ethylene, 4,4'-bis[4-[4-(4-hydroxyphenylsulfonyl)phenoxy]-2-trans-butenyloxy]diphenyl sulfone, 4-[4-[4-(4-hydroxyphenylsulfonyl)phenoxy]-2-trans-butenyloxy]-4'-[4-(4-hydroxyphenylsulfonyl)phenoxy-4-butyloxy]diphenyl sulfone, 4-[4-(4-hydroxyphenylsulfonyl)phenoxy]-2-trans-butenyloxy]-4'-[4-(4-hydroxyphenylsulfonyl)phenoxy-3-propyloxy]diphenyl sulfone, 4-[4-[4-(4-hydroxyphenylsulfonyl)phenoxy]-2-trans-butenyloxy]-4'-[4-(4-hydroxyphenylsulfonyl)phenoxy-2-ethyloxy]diphenyl sulfone, 1,4-bis[4-[4-[4-(4-hydroxyphenylsulfonyl)phenoxy-2-trans-butenyloxy]phenylsulfonyl]phenoxy]-cis-2-butene and 1,4-bis[4-[4-[4-(4-hydroxyphenylsulfonyl)phenoxy-2-trans-butenyloxy]phenylsulfonyl]phenoxy]-trans-2-butene.

3) Compounds where X and/or Y in the formula are saturated or unsaturated hydrocarbons having 1 to 12 carbons and ether bonds;

4,4'-bis[4-(4-hydroxyphenylsulfonyl)phenoxy]dibutyl ether, 2,2'-bis[4-(4-hydroxyphenylsulfonyl)phenoxy]diethyl ether, 4,4'-bis[4-(4-hydroxyphenylsulfonyl)phenoxy-2-ethyleneoxyethoxy]diphenyl sulfone, 2,2'-bis[4-[4-[4-(4-hydroxyphenylsulfonyl)phenoxy-2-ethyleneoxyethoxy]phenylsulfonyl]phenoxy]diethyl ether, 2,4'-bis[2-(4-hydroxyphenylsulfonyl)phenoxy-2-ethyleneoxyethoxy]diphenyl sulfone, 2,4'-bis[4-(2-hydroxyphenylsulfonyl)phenoxy-2-ethyleneoxyethoxy]diphenyl sulfone, 4,4'-bis[3,5-dimethyl-4-(3,5-dimethyl-4-hydroxyphenylsulfonyl)phenoxy-2-ethyleneoxyethoxy]diphenyl sulfone, and 4,4'-bis[3-allyl-4-(3-allyl-4-hydroxyphenylsulfonyl)phenoxy-2-ethyleneoxyethoxy]diphenyl sulfone.

4) Compounds where X and/or Y in the formula are groups represented by Formula (VII);

α, α'-bis[4-(4-hydroxyphenylsulfonyl)phenoxy]-p-xylene, α, α'-bis[4-(4-hydroxyphenylsulfonyl)phenoxy]-m-xylene, α, α'-bis[4-(4-hydroxyphenylsulfonyl)phenoxy]-o-xylene, α, α'-bis[4-[4-[4-(4-hydroxyphenylsulfonyl)phenyl-1,4-phenylenebismethyleneoxy]phenylsulfonyl]phenoxy]-p-xylene, α, α'-bis[4-[4-[4-(4-hydroxyphenylsulfonyl)phenyl-1,3-phenylenebismethyleneoxy]phenylsulfonyl]phenoxy]-m-xylene, α, α'-bis[4-[4-[4-(4-hydroxyphenylsulfonyl)phenyl-1,2-phenylenebismethyleneoxy]phenylsulfonyl]phenoxy]-o-xylene, 4,4'-bis[4-(4-hydroxyphenylsulfonyl)phenyl-1,4-phenylenebismethyleneoxy]diphenyl sulfone, 4,4'-bis[4-(4-hydroxyphenylsulfonyl)phenyl-1,3-phenylenebismethyleneoxy]diphenyl sulfone, 4,4'-bis[4-(4-hydroxyphenylsulfonyl)phenyl-1,2-phenylenebismethyleneoxy]diphenyl sulfone, 4,4'-bis[3,5-dimethyl-4-(3,5-dimethyl-4-hydroxyphenylsulfonyl)phenyl-1,4-phenylenebismethyleneoxy]diphenyl sulfone, 4,4'-bis[3,5-dimethyl-4-(3,5-dimethyl-4-hydroxyphenylsulfonyl)phenyl-1,3-phenylenebismethyleneoxy]diphenyl sulfone, 4,4'-bis[3,5-dimethyl-4-(3,5-dimethyl-4-hydroxyphenylsulfonyl)phenyl-1,2-phenylenebismethyleneoxy]diphenyl sulfone, 4,4'-bis[3-allyl-4-(3-allyl-4-hydroxyphenylsulfonyl)-1,4-phenylenebismethyleneoxy]diphenyl sulfone, 4,4'-bis[3-allyl-4-(3-allyl-4-hydroxyphenylsulfonyl)-1,3-phenylenebismethyleneoxy]diphenyl sulfone and 4,4'-bis[3-allyl-4-(3-allyl-4-hydroxyphenylsulfonyl)-1,2-phenylenebismethyleneoxy]diphenyl sulfone.

5) Compounds where X and/or Y in the formula are groups represented by Formula (VIM;

4,4'-bis[4-(4-hydroxyphenylsulfonyl)phenoxy-2-hydroxypropyloxy]diphenyl sulfone and 1,3-bis[4-[4-[4-(4-hydroxyphenylsulfonyl)phenoxy-2-hydroxypropyloxy]phenylsulfonyl]phenoxy]-2-hydroxypropane.

Of these compounds, preferred are where a is 0 or an integer of 1 to 3, and X and/or Y are —CH$_2$CH$_2$—OCH$_2$CH$_2$— or —CHCH=CHCH$_2$—.

A compound of Formula (V) can be produced using, instead of a compound of Formula (III), a compound represented by Formula (IX)

$$A^1\text{-}X\text{-}A^2 \text{ or } A^3\text{—}Y\text{-}A^4 \qquad (IX)$$

(wherein, A1 to A4 are each independently halogen), according to a method for producing a compound of (I) which is described later. The product is a single compound or a mixture of several compounds. The present invention is applicable to separate or purify these compounds from starting materials and byproducts.

There are no particular restrictions on methods for synthesizing compounds represented by Formula (I) (hereinafter referred to as Compound (I)), except inventions relating to (Composition 15) and (Composition 18). A method for reacting a compound represented by Formula (II) (hereinafter referred to as Compound (II)) with a compound represented by Formula (III) (hereinafter referred to as Compound (III)) in a solvent in the presence of an alkali is exemplified as most preferred.

In Formula (III), X is halogen such as chlorine, bromine or iodine. Actual examples of compounds of Formula (III) include alkyl halides such as methyl iodide, ethyl iodide, ethyl bromide, n-propyl iodide, n-propyl bromide, n-propyl chloride, isopropyl iodide, isopropyl bromide, isopropyl chloride, n-butyl iodide, n-butyl bromide, sec-butyl iodide, sec-butyl bromide, t-butyl iodide, t-butyl bromide, n-pentyl iodide, n-pentyl bromide, n-hexyl iodide and n-hexyl bromide; alkenyl halides such as allyl chloride, allyl bromide, allyl iodide, crotyl chloride and crotyl bromide; cycloalkyl halides such as cyclopropyl iodide, cyclopropyl bromide, cyclopropyl chloride, cyclopentyl iodide, cyclopentyl bromide, cyclopentyl chloride, cyclohexyl iodide, cyclohexyl bromide and cyclohexyl chloride; and aralkyl halides such as benzyl iodide, benzyl bromide, benzyl chloride, 4-chlorobenzyl iodide, 4-methylbenzyl bromide, 3-chlorobenzyl chloride, (1-phenyl)ethyl iodide, (1-phenyl)ethyl bromide, 2-phenylethyl bromide, 2-phenylethyl chloride and 3-phenylpropyl bromide.

Of them, a preferred compound of Formula (III is where X is bromine. It is particularly favorable to use isopropyl bromide. An amount of Compound (III) used is usually in the range of 1 to 3 moles, preferably 1 to 1.5 moles, to a mole of Compound (II).

Actual examples of bases used for the reaction include alkali metal hydroxides such as sodium hydroxide and potassium hydroxide; alkaline earth metal hydroxides such as magnesium hydroxide and calcium hydroxide; alkali metal carbonates such as calcium carbonate; and organic amines such as triethylamine, pyridine and diazabicyclo[5.4.0]unde-7-cene. Of them, alkalis including alkali metal hydroxides such as sodium hydroxide are particularly preferred. An amount of a base used is usually in the range of 1 to 5 moles, preferably 1.5 to 3 moles, to a mole of Compound (II).

Examples of solvents used include water; amides such as N,N-dimethylformamide and N,N-dimethylacetamide; alcohols such as methanol, ethanol and propanol; and two-phase, mixture solvents such as water-toluene, water-xylene and water-benzene. An amount of a solvent used is usually in the range of 0.1 to 10 parts by weight to a part by weight of Compound (II).

A reaction method is, for example, by adding Compound (III) to a solution of an alkali salt of Compound (II). There are no particular restrictions on how to add Compound (III). Examples are a method of dropping a fixed amount of Compound (2) continuously into a reaction solution and adding Compound (III) little by little over several times. A reaction is carried out usually at a temperature between room temperature and the boiling point of the solvent, preferably between 45 to 80° C., and normally finishes in about 1 to 25 hours.

A method for producing a compound of Formula (I) in the present invention is a general term for all processes from starting materials to the completion of a product, covering a reaction process for reacting starting materials to give a reaction mixture containing Compound (I), such as a process for reacting Compound (II) with Compound (III), as well as a purification process, such as separation of the materials and impurities; processes for separating Compound (I) after the completion of the purification process, such as crystallization, distillation, filtration and recrystallization; and processes particularly required for industrial production, such as drying and solvent recovery. Actual examples are a combination of a series of processes of pretreatment, reaction, purification, crystallization, filtration, drying and solvent recovery, and a combination of each process twice or more.

The reaction mixture thus obtained contains Compound (I) as well as impurities such as unreacted Compound (II), unreacted Compound (H) and a byproduct of 4,4'-dihydroxydiphenyl sulfone diether. It is therefore necessary to separate these impurities from the reaction mixture, that is, purification of the reaction mixture, in order to produce the target compound of high purity.

The production method of the present invention is described in detail, using as an example, when a reaction mixture of 4,4'-dihydroxydiphenyl sulfone (hereinafter referred to as BPS) and Compound (III) is purified to isolate the target compound, that is, a compound represented by Formula (V) (hereinafter referred to as Compound (V)).

To react BPS with Compound (III) in the presence of a base, it is usually carried out in a way that, for example, a BSP salt produced from BPS and a base is reacted with Compound (III). Solubility of the BPS salt in non-polar organic solvents is low so that the reaction is usually carried out in a polar solvent, water or a mixed solvent of water and organic solvents. BPS has two positions to form a salt with a base in one molecule. A problem is therefore how to control the production of a byproduct of 4,4'-dihydroxydiphenyl sulfone diether (hereinafter sometimes referred to as the diether) in the reaction.

For example, thanks to the fact that a salt of Compound (V) with a base (alkali) (hereinafter referred to as Compound (V) salt) is less soluble in water than the said di-salt compound is, there is a method that Compound (III) is reacted with the di-salt compound in a saturated or nearly saturated aqueous solution to deposit the Compound (V) salt to remove to the outside of the reaction system as crystals.

Another example is that a reaction is carried out in a two-phase system of water and a water-nonmiscible organic solvent, which dissolves Compound (V) to some extent, pH is controlled to restrain the formation of the said di-salt and Compound (V) salt, and produced Compound (V) is dissolved in the organic solvent to remove into the outside of the system.

In either method, after the reaction is completed, the reaction mixture contains impurities of BPS, the diether and others. If such impurities are contained, it is difficult to isolate the target compound of high purity as crystals only by operations such as recrystallization, because the structures of the impurities are similar to that of the target compound. A method is applied for separating the impurities by pH adjustments, as BPS, Compound (V) and the diether are different in acidity.

An operation of purifying the said reaction mixture to isolate the target compound is carried out, for example, according to steps described below:

(a) First, remove unreacted Compound (III).

The reaction solution usually contains unreacted Compound (III). Compound (III) is generally unstable in water, particularly in an aqueous alkaline solution, and is more unstable and easily decomposes when heated. As described above, when water is used as a reaction solvent and an alkali as a base, Compound (III) has to be used in an excessive amount because of its easy decomposition during the reaction. Compound (III) decomposes to generate an acid if it is present in post-treatment processes, such as purification, after the reaction is completed. The acid reacts with the alkali to reduce pH of the reaction solution.

The pH reduction is local and its change is small. An accurate pH adjustment is however particularly required, as described later, in order to separate the target compound into the organic layer and impurities into the aqueous alkali layer precisely. Non-uniform pH values or pH values different from preset values result in difficulties in complete separation of the target compound from starting materials and byproducts.

In this reaction, the reaction solution was sometimes colored in the process for purifying the reaction solution after the reaction was completed and the product, Compound (V), also colored. Once the product is colored, a problem is difficulties in decoloring.

The inventors have studied causes of the coloring in detail. As a result, it was considered that a reason why the reaction solution was colored in the purification process was because heavy metal ions, such as iron ions, contained in industrial water used as a reaction solvent and as water in the purification process or dissolved from an SUS reaction tank, formed chelate compounds with compounds having phenolic hydroxyl groups, such as Compound (V), and the chelate compounds were the cause of the coloring. It was also considered that the chelate compounds, which caused coloring, were easily formed because the pH value of the reaction solution lowered locally to produce a pH region where a compound having a phenolic group could form a chelate compound with a heavy metal ion. It is therefore necessary to control pH precisely and uniformly in the purification process in order to efficiently prevent the formation of the chelate compounds and to produce non-colored products.

The present invention has made it possible to prevent the pH value of the reaction solution from changing due to the decomposition of Compound (III) so as to adjust the pH accurately, by providing a process for removing unreacted Compound (III) contained in the reaction solution in the process for purifying the reaction solution after the reaction is completed.

Compound (III) may be removed after the completion of the reaction and before the isolation of the target compound. In the present invention, it is favorable to remove Compound (III) after the completion of the reaction and before the said pH adjustment of the aqueous layer, from the viewpoint of accurate pH adjustment with control of pH changes to the minimum. It is more favorable to remove unreacted Compound (III) after the reaction is completed and before the diether is extracted with organic solvents for removal. In other words, it is preferable to provide the process for removing Compound (III) immediately after the reaction process.

There are no particular restrictions on methods for removing Compound (III). Examples include (1) after the reaction is completed, the reaction solution is heated to evaporate Compound (III) to remove; and (2) after the reaction is completed, an extract solvent, such as benzene or toluene, is added to the reaction solution to extract Compound (III) to remove.

Of them, Method (1) is simpler in the present invention. In the operation of evaporating for removal in Method (1), it is preferable to distill out Compound (III) together with the solvents used for the reaction. Particularly when water is used as a reaction solvent, it is favorable to add a solvent azeotropic with water, such as toluene or benzene, and to distill out Compound (III) together with the mixed solvent, because Compound (III) can be recovered at a lower temperature with the minimum decomposition. Method (1) can be carried out at the atmospheric pressure or under reduced pressure. If performed under reduced pressure, unreacted Compound (III) can be evaporated to remove at a lower temperature so that pH changes due to the decomposition of Compound (III) can be controlled.

Compound (III) removed from the reaction solution may be recovered or obtained by other means for reuse.

In the production method of Compound (I) with a process for removing Compound (III) after Compound (II), such as BPS, and Compound (III) are reacted in 0.3 to 1.5 parts by weight of an aqueous solvent to a part by weight of Compound (II) in the presence of 1.5 to 3 moles of an alkali to a mole of Compound (II) followed by distillation of Compound (III), if Compound (III) is heated to distill out and then water is further added to distill Compound (III) to remove, the compound is efficiently recovered and production of impurities, such as the diether, can be controlled.

It is favorable to add water separately over several times. In addition, an amount of water added at the beginning is in the range of 0.03 and 0.1 parts by weight, more preferably 0.04 and 0.08 parts by weight, to a part by weight of Compound (II). A favorable way is to control an amount of water added at the beginning for a sufficient recovery of Compound (III). If less than 0.03 parts by weight, Compound (III) cannot be distilled out sufficiently. If exceeds 0.1 parts by weight, impurities, such as the diether, are more produced. An amount of water added at the second time and after may be the same as that at the beginning, or larger if Compound (III) remains in small amount.

The smaller an amount of Compound (III) remains in the reaction solution after Compound (III) is distilled out, the more preferable. It becomes more difficult to completely remove the compound by distillation with a larger reaction scale. Compound (III) remaining in the reaction solution after distillation may be contained, for example, in an organic solvent used in the process for crystallizing Compound (I) (Compound (V)) from the organic solvent, via post processes. The organic solvent used for the crystallization is often recovered for reuse after Compound (I) is filtrated. Reuse of the solvent containing a large amount of Compound (III), as described above, causes problems such as coloring of Compound (I) because of decomposition of Compound (III) in various processes. It is therefore necessary to reduce the amount of Compound (III) in the organic solvent. It is usually preferable to control to 1% by weight or less. It is favorable to distill out Compound (III) so that the content of Compound (III) in the organic solvent used in the crystallization process is 1% by weight or less.

(b) Next, a water-nonmiscible solvent and, if required, water and/or an alkali (aqueous) are added to the reaction mixture to make a two-phase solution of organic and aqueous layers. When a polar solvent is used for the reaction, it is preferable to carry out this operation after the polar solvent is recovered or removed. It is also favorable to adjust pH to 8 or above to completely separate the diether from the Compound (V) salt. There are no particular restrictions on the said water-nonmiscible solvents if they are organic solvents that do not mix with water. Aromatic hydrocarbons such as toluene, xylene and benzene are preferably used. The separation operation separates the diether having no phenolic hydroxyl group into the organic layer and the target compound into the aqueous layer.

The separation operation is favorably carried out at a temperature above the crystallization temperature, usually in the temperature range of 70 and 90° C., from the viewpoint of preventing the target compound, impurities and the like from crystallizing. An amount of the water-nonmiscible organic solvent used is usually in the range of 0.5 and 5 ml to 1 g of BPS used as a starting material. Compound (V) produced and unreacted BPS are both soluble, but the diether is insoluble, in aqueous alkaline solutions. Without using a water-nonmiscible organic solvent, the diether can be removed in a way that a reaction mixture obtained after organic solvents and the like are removed (or after the reaction is completed if water is used as a reaction solvent) is adjusted pH to 8 or above and deposited diether is filtered off.

(c) Then, the aqueous layer containing the target compound is separated. A water-nonmiscible organic solvent and, if required, water are added to the obtained aqueous layer to make a two-phase solution of organic and aqueous layers. The aqueous layer is adjusted pH to a preset value (P1). The adjustment of pH to the preset value (P1) separates the target compound into the organic layer and impurities including BPS into the aqueous alkali layer. The pH value is usually adjusted by adding an acid or alkali to the aqueous layer. In this case, after the pH of the aqueous layer is adjusted, a water-nonmiscible organic solvent may be added to extract the target compound.

Examples of acids for use include hydrochloric acid, sulfuric acid and nitric acid. Sodium hydroxide and potassium hydroxide are exemplified as alkalis for use. An alkali, when used, can be added in a form of aqueous solution. It is preferable to add an acid or alkali little by little in amount while sufficiently stirring the whole mixture from the viewpoint of prevention of drastic pH changes and precise pH adjustment. The preset value (P1) of pH is usually in the range of 8 and 9, preferably 8.3 and 8.7. In this case, to prevent the target compound and impurities from crystallizing, it is favorable to add a water-nonmiscible organic solvent and water, as required, to the reaction solution and to carry out the separation operation while keeping a temperature above the crystallization temperature, usually in the range of 70 and 90° C.

(d) Furthermore, water and, if required, a water-nonmiscible organic solvent are added to the organic layer obtained after the said aqueous layer is removed, to make again a two-phase solution, and the aqueous layer is adjusted pH to a preset value (P2). Particularly when the reaction mixture is high in concentration, a third layer in which the target compound is not completely separated from BPS and others may be formed near the interface between the organic and aqueous layers. In this case, it is necessary to remove the completely separated aqueous layer, and the remaining organic and third layers are adjusted pH for completely separating BPS from the target compound.

In the prior art, water and a water-nonmiscible organic solvent are added to a reaction product containing the target compound to make a two-phase solution, pH of the aqueous layer is adjusted to a preset value to separate the organic layer, and the target compound is obtained from the organic layer. However, particularly when a reaction mixture of high concentration is purified, for example, when a reaction mixture obtained from a reaction of materials of high concentrations or a reaction mixture containing a high concentration of inorganic salt is purified without diluting it much, it has been difficult to separate the target compound from impurities with only one pH adjustment.

The inventors have studied causes of the above difficulty. As a result, the following were considered to be causes of the difficulty in the complete separation of the target compound from impurities:

(1) A difference in acidity between the phenolic hydroxyl groups of Compound (V) and BPS is small. Therefore, it is impossible to separate the target compound from BPS and others completely without an accurate pH adjustment.
(2) Solubilities of both of the target compound and BPS in water and water-nonmiscible solvents are relatively small. Because of this, when a water-nonmiscible solvent is added to a mixture of these to make a two-phase solution, particularly when a solution of the mixture of high concentration is used, a third, intermediate layer in which Compound (V) and BPS are mixed without being separated is formed near the interface between the aqueous and organic layers. Therefore, their separation is insufficient. A ratio of the layer in the whole solution tends to become larger as a reaction product is higher in concentration.
(3) Due to the effect of salting out by a large amount of inorganic salts produced from the reaction of Compound (III) with BPS, BPS salts do not dissolve in the aqueous layer completely and cannot dissolve in the organic layer either so as to take Compound (V) in to form the third layer.
(4) On the other hand, when the target compound is produced at an industrial scale, fairly large amounts of water and a water-nonmiscible organic solvent cannot be added to the reaction solution because of work efficiency and capacities of reaction and treatment tanks.
(5) Therefore, it may be often the case that it is difficult to completely separate the target compound, Compound (V), from BPS when a series of operations of adjusting pH of the aqueous layer to be treated to a preset value and separating the organic layer is carried out only once.

Based on the above facts, in the present invention, a series of operations consisting of a pH adjustment of the aqueous layer of the two-phase solution and separation of the organic layer is repeated several times in order to produce the target compound of high purity in high yield.

The present invention provides methods for producing 4,4'-dihydroxydiphenyl sulfone monoethers, in which the target compound of high purity is isolated efficiently from a mixture even if the mixture contains the target compound and impurities of high concentrations.

When the reaction product obtained from a reaction of BPS with a compound of Formula (III) in a solvent in the presence of a base is purified, only a requirement is an addition of the operations of the pH adjustment of the aqueous layer of the two-phase solution and separation of the organic layer, without changing the current production lines at all.

Therefore, according to the purification method of the present invention, 4,4'-dihydroxydiphenyl sulfone monoethers of extremely high purity can be produced advantageously in industrial production.

The second pH adjustment can be done by an operation similar to that of the first. An adjustment of pH of the aqueous layer to a preset value (P2) removes impurities contained in the organic layer into the aqueous layer. The pH value (P2) can be set to the same value as that of P1. It is however preferable to set P2 very slightly different from the pH value of the first adjustment in order to completely separate the target compound from BPS. Setting P2 to a value lower than P1 is preferred. For example, P1 is set in the range of 8.4 and 8.7 and P2 in the range of 8.3 and 8.6. A series of the operations of the pH adjustment of the aqueous layer of the two-phase solution and separation of the organic layer can be repeated further, if required.

As described above, if a series of the operations of adjusting pH of the aqueous layer to the preset values (P1 and P2) and separating the organic layer is repeated twice or more in the process for purifying the reaction solution, 4,4'-dihydroxydiphenyl sulfone monoethers of extremely high purity can be isolated from the reaction mixture.

In the process of purification with water and an organic solvent for removing impurities, other than Compound (I), from the reaction solution, as described above, by adjusting pH of the reaction solution produced from the reaction of Compound (II) with Compound (III) in a solvent in the presence of a base, it is preferable to set a concentration of the compound of Formula (III) in the organic solvent to 5% by weight or less, more preferably 2% by weight or below, and furthermore preferably 1% by weight or less. An organic solvent used for a purification process such as that mentioned above, is often an organic solvent, for example, that is used in a crystallization process and recovered for reuse. In this case, the solvent may contain compounds involved in the reaction. Of them, Compound (III) easily decomposes when contacts with water, alkali or the like. Use of an organic solvent containing such a compound for a purification process may cause problems including coloring of Compound (I). It is necessary to reduce the content of such an impurity as much as possible. To reduce an amount of Compound (III) contained in an organic solvent to be used in the purification process, a new organic solvent can be used instead of a recovered organic solvent for reuse. A recovered solvent after precision distillation may be also used. For an efficient production overall, however, it is preferable to distill out unreacted Compound (III) to the outside of the system as much as possible so as not to remain any, in the process for distilling Compound (III) to remove.

(e) Finally, the organic layer is separated from the two-phase solution after the final pH adjustment is carried out, washed with water if necessary, and cooled to deposit crystals. The crystals are separated by filtration, washed with water and dried to give the target compound.

Compound (I) may often form a molecular compound particularly with a crystallization solvent in the crystallization process for taking out the compound as crystals, because of its structural and electronic properties. If Compound (I) forming a molecular compound with the crystallization solvent or the like is filtrated and then heated to dry under reduced pressure while leaving to stand, the compound may melt simultaneously when the crystalline form as the molecular compound collapses, and form amorphous block particles with surrounding crystals in the condition of keeping the solvent inside, halfway through the process that the solvent breaks the bond with Compound (I) and vaporizes. There is no problem if the compound melts at a temperature above the melting point of Compound (I), because Compound (I) itself does not crystallize even if releasing the solvent molecule. In case of melting below the melting point of Compound (I), Compound (I) crystallizes after the molecular compound melts and the solvent vaporizes. Because of this, it is often the case that part of the solvent does not vaporize completely and is taken in the inside of block particles. It is very difficult to pulverize such block particles unless considerable force is applied from the outside. The solvent taken in the inside cannot be removed completely.

Therefore, the present invention is characterized in drying with mechanical stir. It is particularly favorable to dry by heating under reduced pressure with mechanical stir.

Actual examples of solvents to form molecular compounds with Compound (I) include water; alcohols such as methanol, ethanol, n-propanol, isopropanol and 1,2-butanediol; ketones such as acetone, methyl ethyl ketone and acetyl acetone; nitrites such as acetonitrile and benzonitrile; ethers such as diethyl ether, dibutyl ether, tetrahydrofuran and dioxane; esters such as methyl acetate, ethyl acetate and butyl acetate; amides such as N,N-dimethylformamide and N,N-dimethylacetamide; halogenated hydrocarbons such as dichloromethane, chloroform, 1,2-dichloroethane and chlorobenzene; aromatic hydrocarbons such as dimethyl sulfoxide, benzene, toluene and xylene; and aliphatic hydrocarbons such as hexane, cyclohexane and decalin. Particularly, a molecular compound formed with an aromatic hydrocarbon, such as benzene or toluene, is preferably dried according to the method of the present invention, because the compound is apt to melt during this process.

There are no particular restrictions on a ratio of Compound (I) and a solvent that form a molecular compound. Concretely, the ratio is in the range of 0.1 to 10 moles of a solvent to a mole of Compound (I).

In the present invention, "mechanical stir" refers to stirring a molecular compound with a stirring apparatus. Actual examples of stirring apparatus include those with stirring blades such as inclined paddle blades, flat paddle blades, propeller blades, anchor blades, faudler blades, turbine blades, bull margin blades, max blend blades, full zone blades, ribbon blades, super mix blades or inter mig blades; and those with rotary disks such as disk, notched disk or screw.

A vacuum stirring apparatus with a stirring apparatus may be of batch or continuous type. Actual examples include Paddle Dryer (made by Nippon Kansoki Co., Ltd), Multifin Processor (made by Nara Kikai Seisakusho Co., Ltd), Plough Share Mixer (made by Taiheiyo Kiko Co., Ltd) and Inklandent Dryer (made by Tukishima Kikai Co., Ltd).

A stirring speed depends on a type of stirring apparatus used and other conditions. Approximately 1 to 10 revolutions/ minute is usually satisfactory.

A heating temperature differs, depending on a type of solvent to vaporize. For example, when toluene is used, it is preferably in the range of room temperature and 100° C., and particularly favorably from 50 to 90° C.

Drying under reduced pressure is usually carried out at 200 mmHg or below, and preferably 150 mmHg or less in particular.

The content of the solvent before and after drying can be measured by such a means as calorimetric analysis and differential thermal analysis.

The present invention is characterized in use of a solvent, particularly water, containing 0.05 ppm or less of iron components in the process for producing Compound (I). It is preferable to use a solvent, such as water, containing a very small amount of iron components throughout the production processes. However, it is not always necessary to use it in all processes. As described above, an iron component can form a complex with Compound (I) particularly when pH is between 5 and 7. It is therefore favorable to use water containing a very small amount of iron components particularly in the process where pH control is difficult. Thus, use of a solvent, such as water, containing a very small amount of iron components is preferred in the reaction process for producing Compound (I) and/or in the purification process for removing compounds, other than Compound (I), from the reaction mixture containing Compound (I). In the present invention, "an amount of iron components contained" refers to a content of iron, iron compounds and iron ions (including ions with iron atoms) in water used and the like. These iron components, in the form existing in water and the like or reacting with acids or alkalis to become iron ions or ions containing iron atoms, can form colored complexes with Compound (I).

Examples of methods for obtaining a solvent containing 0.05 ppm or less of iron components include known methods in the art, such as, in the case of water, distillation of industrial water (distilled water), and purification of industrial water through columns filled with substances having a function to catch iron components, such as ion exchange resins (water passed through a water purifier, ion exchanged water and the like). An amount of iron components contained in water can be measured with such measuring equipment as UV or visible light spectrophotometer, inductively coupled high-frequency plasma-atomic emission spectroscope, atomic absorption analyzer, photoelectric photometer and calorimeter.

The present invention is characterized in production of Compound (I) using reaction or purification tanks with corrosion-resistant layers on the inner walls (which may hereinafter refer to as "Tanks"). It is preferable to use tanks with corrosion-resistant layers throughout the production processes. However, it is not always necessary to use them in all processes. It is efficient to use Tanks when there is a risk of elution of iron components and the like, which cause coloring of Compound (I), from a tank into the solution due to corrosion. It is therefore preferable to use reaction tanks with corrosion-resistant layers in the reaction process for producing Compound (I) and/or in the purification process for removing compounds, other than Compound (I), from the reaction mixture containing Compound (I).

There are no particular restrictions on materials used for the corrosion-resistant layers, if they are not corroded with acids, such as sulfuric acid, or alkalis, such as sodium hydroxide, used in the reaction or purification process.

Examples of corrosion-resistant materials include corrosion-resistant metals such as titanium, zirconium, tantalum, niobium and nickel; glasses such as borosilicate glass, neutral glass, quartz glass and alkali-resistant glass; inorganic materials such as enamel; organic materials including fluorine resins such as ethylene tetrafluoride resins (PTFE or TFE), ethylene tetrafluoride-perfluoroalkoxy vinyl ether copolymers (PFA), ethylene tetrafluoride-propylene hexafluoride copolymers (FEP), polychlorotrifluoroethylene (PCTFE), ethylene tetrafluoride-ethylene copolymers (ETFE), chlorotrifluoroethylene-ethylene copolymers (ECTFE), polyvinylidene fluoride (PVDF) and polyvinyl fluoride (PVF).

An example of a method for forming a corrosion-resistant layer on the inner wall is lining or coating of a corrosion-resistant material on the inner wall. As for methods for lining or coating, when a glass is used, an example is glass lining that a vitreous glaze is baked on the surface of the base material (steel plate) composing the tank. When a fluorine resin is used, coating by baking a powder and sheet lining using a glass cloth are exemplified. Of them, a tank whose inner wall is lined or coated with a glass or fluorine resin is preferably used from the viewpoint of heat resistance, durability and others. It is more favorable to use a tank with the inner wall lined with a glass (commonly known as GL).

In the present invention, any of the following methods are applicable: (a) a reaction is carried out in an SUS tank as before, using water with a content of iron components of 0.05 ppm or less as a reaction solvent and/or purification solvent; (b) a reaction is carried out in a tank with a corrosion-resistant layer on the inner wall, using industrial water as before; or (c) water containing 0.05 ppm or less of iron components is used as a reaction solvent and/or a purification solvent and a tank with a corrosion-resistant layer on the inner wall also used. The method (c) is particularly preferred from the viewpoint of production of non-colored, highly pure diphenyl sulfone compounds more securely.

The reaction mixture may be colored in the purification process for removing compounds, other than Compound (I), from the reaction mixture containing Compound (I). This is considered to occur because metal ions including iron ions, nickel ions and chromium ions, that dissolve out from an SUS reaction vessel, which is usually used as a reaction vessel, in the process for reacting Compound (II), such as BPS, with Compound (III), or that are contained in a very small amount in water (industrial water) used in the process for purifying the reaction mixture, combine with phenolic compounds, such as Compound (I), to form complexes, which color the reaction solution. It is difficult to decolor the solution, once colored, even if purified repeatedly afterward. Because of this, in the present invention, a chelating agent is added to the reaction mixture in the process for purifying the reaction mixture, and captures the metal ions by chelation for preventing the coloring.

There are no particular restrictions on chelating agents used, if they are compounds to bind with metal ions to form chelates. Actual examples include compounds obtained from reactions of compounds having amino groups, such as ammonia, polyamine and amino acids, with carbon disulfide, halogenated carboxylic acids, halogenated alcohols and the like; and salts of these compounds; and dithiocarbamates; dimethylglyoxime; dithizone, bipyridine and phenanthroline.

Examples of the said polyamines include ethylenediamine, N-methylethylenediamine, N,N'-dimethylethylenediamine, 1,2-diaminopropane, 1,3-diaminopropane, diethylenetriamine, triethylenetetramine, tetramethylenepentamine and pentamethylenehexamine.

Examples of halogenated carboxylic acids include monochloroacetic acid, monobromoacetic acid, monoiodoacetic acid, 1-chloropropionic acid, 2-chloropropionic acid, 1-bromopropionic acid and 2-bromopropionic acid.

Examples of halogenated alcohols include 1-chloroethanol, 2-chloroethanol, 1-bromoethanol, 2-bromoethanol, 1-chloropropanol, 2-chloropropanol, 2-chloroisopropanol, 3-chloropropanol, 1-bromopropanol, 2-bromopropanol, 2-bromoisopropanol and 3-bromopropanol.

Actual examples of chelating agents include dithiocarbamates such as sodium dithiocarbamate and potassium dithiocarbamate; acetic acid derivatives of amines such as ethylenediaminetetraacetic acid (EDTA), hydroxyethyliminodiacetic acid (HIDA), nitrilotriacetic acid (NTA), hydroxyethylethylenediaminetriacetic acid (HEDTA), diethylenetriaminepentaacetic acid (DTHA) and triethylenetetraminehexaacetic acid (TTHA); and salts of these acetic acid derivatives (for example, alkali metal salts such as sodium and potassium; alkaline earth metal salts such as calcium and magnesium; and ammonium salts); ethanolamines such as ethanolamine, N,N'-bis(2-hydroxyethyl)ethylenediamine, N,N',N'''-tris(2-hydroxyethyl)ethylenediamine and dihydroxyethylglycine (DHEG); salts of dithiocarbamic acid derivatives of polyamines such as N,N'-bis(dithiocarboxy)ethylenediamine sodium salt, N,N'-bis(dithiocarboxy) ethylenediamine potassium salt, N,N'-bis(dithiocarboxy)trimethylenediamine sodium salt, N,N'-bis(dithiocarboxy) trimethylenediamine potassium salt, N,N'-bis (dithiocarboxy)diethylenetriamine sodium salt, N,N'-bis (dithiocarboxy)diethylenetriamine potassium salt, N,N',N''-tris(dithiocarboxy)diethylenetriamine sodium salt, N,N',N''-tris(dithiocarboxy)diethylenetriamine potassium salt, N,N'-bis(dithiocarboxy)triethylenetetramine sodium salt, N,N'-bis (dithiocarboxy)triethylenetetramine potassium salt, N,N',N''-tris(dithiocarboxy)triethylenetetramine sodium salt and N,N',N''-tris(dithiocarboxy)triethylenetetramine potassium salt; dimethylglyoxime, dithizone, bipyridine and phenanthroline.

Of these chelating agents, preferred are cheltating agents forming water-soluble chelates (water-soluble chelating agents) represented by chelating agents obtained by reacting ammonia or polyamine with halogenated carboxylic acids and/or halogenated alcohols; and salts of these agents. Use of EDTA or its salts is particularly preferred because of easy acquisition, handling, easy separation and the like.

Examples of EDTA salts include EDTA disodium salt, EDTA trisodium salt, EDTA tetrasodium salt, EDTA dipotassium salt, EDTA tripotassium salt, EDTA tetrapotassium salt, EDTA calcium salt, EDTA tricalcium salt, EDTA diammonium salt and EDTA magnesium dipotassium salt. When a water-soluble chelating agent is added to the reaction mixture, the chelates produced are water-soluble and are not taken in the crystals of 4,4'-dihydroxydiphenyl sulfone. Thus, the target compound that is completely decolored is produced.

A chelating agent can be added at any one of the following stages: (a) after the completion of the reaction and before the removal of unreacted Compound (III), (b) after the removal of Compound (III) and before the removal of 4,4'-dihydroxydiphenyl sulfone diethers, (c) after the removal of 4,4'-dihydroxydiphenyl sulfone diethers and before the removal of unreacted Compound (II) with pH adjustments, and (d) after the removal of unreacted Compound (II) with pH adjustments. Of them, (d) is preferred, that is, a chelating agent is added after pH is adjusted to remove unreacted Compound (II). An addition of a water-soluble chelating agent at the same time when water is added to the reaction mixture is particularly preferred because metal ions in water are chelated to form water-soluble chelates for easy separation. A chelating agent can be added over several times, if required. A chelating agent is usually used in an aqueous solution. An addition amount of the agent may be determined properly depending on the content of metal ions, such as iron ion, nickel ion and chromium ion, in the reaction mixture. If an amount of a chelating agent added is too small, a coloring prevention effect by the addition of the chelating agent is unsatisfactory. On the other hand, if the agent is added too much, the coloring prevention effect is satisfactory but an excessive amount of the chelating agent may be mixed in the final product of Compound (I) as an impurity. It is therefore favorable to measure a concentration of metal ions contained in the reaction mixture by a known method before the agent is added, and then add an amount of chelating agent corresponding to the concentration of metal ions. An addition amount of a chelating agent is usually from 0.0001 to 0.5 parts by weight, preferably from 0.001 to 0.1 parts by weight, to 100 parts by weight of the reaction mixture.

The inventions relating to the aforementioned (Composition 7), (Composition 15), (Composition 18), (Composition 24), (Composition 26), (Composition 27), (Composition 28) and (Composition 31) are favorably used as methods to produce Compound (I) that has a b value of 2.5 or less when measured by a color difference meter or that is visually white. Compound (I) is preferably whiter as a product when used as a developer. Production methods of the prior art have a problem of impossibility to supply such a product stably. The problem is solved with use of the methods of the present invention.

BEST FORMS TO IMPLEMENT THE INVENTION

The present invention is described in detail in reference to Examples. The present invention is not limited to the following examples. Compound (II), types of solvents, types of tanks used in the reaction and purification processes and other conditions can be changed at discretion as long as they are not deviated from the points of the invention.

Distilled water was used in Reference Example 1, Examples 1 to 3 and Comparative Examples 1 to 4. The content of metal ions in the distilled water, measured by an inductively coupled plasma-atomic emission spectroscope, was 0.05 ppm or less.

In Reference Example 1, Examples 1 to 3 and Comparative Examples 1 to 4, tanks with the inner walls lined with glass (hereinafter referred to as GL tanks) were used as reaction and purification tanks.

REFERENCE EXAMPLE 1

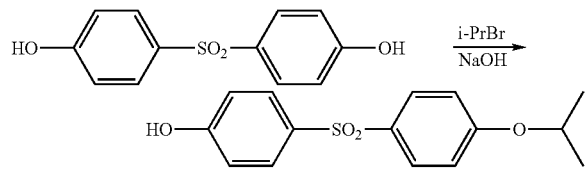

450 g of 4,4'-dihydroxydiphenyl sulfone (BPS), 255 ml of a 48% aqueous solution of sodium hydroxide and 120 ml of water were placed in a reaction tank, and mixed with stirring to make the whole solution homogeneous, while temperature rose to 75° C. 225 g of isopropyl bromide was slowly dropped into the obtained solution at 55±3° C. The resulting solution was continuously stirred, after the completion of the dropping, at 55±5° C. for 20 hours in total from the beginning of the dropping. The obtained reaction solution was used to purify in Example 1 and Comparative Example 1.

EXAMPLE 1

Purification of the Mixture Containing 4-isopropoxy-4'-hydroxydiphenyl Sulfone and Impurities (Composition (1) to (Composition 6)

235 ml of warm water was added to the reaction solution and heated at 80° C. for an hour to evaporate unreacted isopropyl bromide to remove. Then, 300 ml of warm water and 250 ml of toluene were added at 80° C. to stir sufficiently. The aqueous layer was separated.

(1) First pH Adjustment

To the obtained aqueous layer were added 1100 ml of toluene and 200 ml of water at 79° C., and stirred at the same temperature for 30 minutes. Further, 30% dilute sulfuric acid was dropped little by little with stirring at 82° C. over an hour, to adjust pH of the aqueous layer of the reaction solution uniformly to 8.4 to 8.7. The resulting solution was left to stand at 82° C. for 30 minutes and the toluene layer was separated.

(2) Second pH Adjustment

To the obtained toluene layer were added 300 ml of toluene and 300 ml of water at 82° C., and 30% dilute sulfuric acid was dropped little by little with stirring at 82° C. over an hour, to adjust pH of the aqueous layer uniformly to 8.3 to 8.6. The resulting solution was left to stand at 82° C. for 30 minutes and the toluene layer was separated.

To the toluene layer were added 250 ml of toluene and 250 ml of water at 82° C., and stirred at the same temperature for 2 hours. Then, the resulting solution was left to stand at 82° C. for 30 minutes and the toluene layer was separated. The obtained toluene layer was cooled to deposit crystals. The crystals were separated by filtration, washed with toluene and dried to give 368.0 g of the target compound, 4-isopropoxy-4'-hydroxydiphenyl sulfone, as powder (yield: 70%).

An analysis of the product for purity by high-performance liquid chromatography showed 99.83% by weight of 4-isopropoxy-4'-hydroxydiphenyl sulfone and 0.01% by weight of BPS.

COMPARATIVE EXAMPLE 1

Purification of the Mixture Containing 4-isopropoxy-4'-hydroxydiphenyl Sulfone and Impurities Comparative Example against Example 1

235 ml of warm water was added to the reaction solution obtained in Reference Example 1 and heated at 80° C. for an hour to evaporate unreacted isopropyl bromide to remove. Then, 300 ml of warm water and 250 ml of toluene were added at 80° C. to stir sufficiently. The aqueous layer was separated.

To the obtained aqueous layer were added 1100 ml of toluene and 200 ml of water at 79° C., and stirred at the same temperature for 30 minutes. Further, 30% dilute sulfuric acid was dropped little by little with stirring at 82° C. over an hour, to adjust pH of the aqueous layer uniformly to 8.4 to 8.7. The resulting solution was left to stand at 82° C. for 30 minutes and the toluene layer was separated.

To the toluene layer were added 250 ml of toluene and 250 ml of water at 82° C., and stirred at the same temperature for 2 hours. Then, the resulting solution was left to stand at 82° C. for 30 minutes and the toluene layer was separated.

The obtained toluene layer was cooled to deposit crystals. The crystals were separated by filtration, washed with toluene and dried to give 368.0 g of the target compound, 4-isopropoxy-4'-hydroxydiphenyl sulfone, as powder (yield: 70%).

An analysis of the product for purity by liquid chromatography showed 98.4% by weight of 4-isopropoxy-4'-hydroxydiphenyl sulfone and 1.5% by weight of BPS.

EXAMPLE 2

Example for (Composition 15) to (Composition 17)

450 g of 4,4'-dihydroxydiphenyl sulfone (BPS), 255 ml of a 48% aqueous solution of sodium hydroxide and 120 ml of water were placed in a reaction tank and mixed with stirring to make the whole solution homogeneous, while temperature rose to 75° C. 225 g of isopropyl bromide was slowly dropped into the obtained solution at 55±3° C. The resulting solution was continuously stirred, after the completion of the dropping, at 55±5° C. for 20 hours in total from the beginning of the dropping.

235 ml of warm water was added to the reaction solution and heated at 80° C. for an hour to evaporate unreacted isopropyl bromide to remove. Then, 300 ml of warm water and 250 ml of toluene were added at 80° C. to stir sufficiently. The aqueous layer was separated.

To the obtained aqueous layer were added 1100 ml of toluene and 200 ml of water at 79° C., and stirred at the same temperature for 30 minutes. The toluene used at this time was toluene recovered from that used for the crystallization of 4-isopropoxy-4'-hydroxydiphenyl sulfone. The content of isopropyl bromide in the toluene layer was 0.5% by weight. Further, 30% dilute sulfuric acid was dropped little by little with stirring at 82° C. over an hour, to adjust pH of the aqueous layer of the reaction solution uniformly to 8.4 to 8.7. The resulting solution was left to stand at 82° C. for 30 minutes and the toluene layer was separated.

To the obtained toluene layer were added 300 ml of toluene and 300 ml of water at 82° C., and 30% dilute sulfuric acid was dropped little by little with stirring at 82° C. over an hour, to adjust pH of the aqueous layer uniformly to 8.3 to 8.6. The resulting solution was left to stand at 82° C. for 30 minutes and the toluene layer was separated.

To the toluene layer were added 250 ml of toluene and 250 ml of water at 82° C., and stirred at the same temperature for 2 hours. Then, the resulting solution was left to stand at 82° C. for 30 minutes and the toluene layer was separated. The obtained toluene layer was cooled to deposit crystals. The crystals were separated by filtration, washed with toluene and dried to give 368.0 g of the target compound, 4-isopropoxy-4'-hydroxydiphenyl sulfone, as powder (yield: 70%).

An analysis of the product for purity by high-performance liquid chromatography showed 99.83% by weight of 4-isopropoxy-4'-hydroxydiphenyl sulfone and 0.01% by weight of BPS. A measurement of the product by a color-difference meter (made by Nippon Denshoku Kogyo Co., Ltd, Model: 1001 DP) showed that the b value was 2.5 or less. No coloring was observed.

COMPARATIVE EXAMPLE 2

Comparative Example Against Example 2

Example 2 was repeated, except that recovered toluene was added to adjust pH and the content of isopropyl bromide in the toluene layer was 5.5% by weight, to give 4-isopropoxy-4'-hydroxydiphenyl sulfone with the same yield and purity. The product was however visually colored yellow.

EXAMPLE 3

Example for (Composition 7) to (Composition 14)

210 g of BPS, 74.2 ml of a 48% aqueous solution of sodium hydroxide and 740 ml of water were placed in a reaction tank, and mixed with stirring to make the whole solution homogeneous, while temperature rose to 80° C. 705 ml of toluene was added to the obtained solution at 70° C. and 165 g of isopropyl bromide (iPr-Br) was dropped with stirring. The resulting solution was stirred at 76 to 80° C. for 8 hours. Then, 4.8 ml of a 48% aqueous solution of sodium hydroxide and 22 g of isopropyl bromide were added and stirred at 78 to 80° C. for 6 hours. Further, 3.3 ml of a 48% aqueous solution of sodium hydroxide and 25 g of isopropyl bromide were added and reacted at 78 to 81° C. for 8 hours.

After the reaction was completed, 300 ml of toluene was added to the reaction solution and heated at 80° C. for 3 hours to evaporate unreacted isopropyl bromide to remove completely.

Then, 200 ml of water, 694 ml of toluene, 2.5 g of anhydrous sodium carbonate (soda ash) and 10 ml of warm water were added to the reaction solution, and further a 48% aqueous solution of sodium hydroxide was added to adjust pH of the reaction solution to 8.55±0.02. The resulting solution was left to stand for 30 minutes and the toluene layer was separated. To the toluene layer were added 500 ml of water and 800 ml of toluene at 75 to 80° C. The resulting solution was stirred at the same temperature for 30 minutes, and left to stand for 30 minutes. The toluene layer was separated and cooled. The deposited crystals were separated by filtration, washed with water and dried to give 171.7 g of the target compound, 4-isopropoxy-4'-hydroxydiphenyl sulfone, as powder (yield: 70%). At this time, an amount of isopropyl bromide contained in the toluene layer was analyzed by gas chromatography, being 0.5% by weight.

The obtained 4-isopropoxy-4'-hydroxydiphenyl sulfone was 99% or more in purity, and had a b value of 2.5 or less when measured by a color-difference meter (made by Nippon Denshoku Kogyo Co., Ltd, Model: 1001 DP). No coloring was observed.

EXAMPLE 4

Example for (Composition 18) to (Composition 23)

450 g of BPS, 255 ml of a 48% aqueous solution of sodium hydroxide and 120 ml of water were placed in a reaction tank, and mixed with stirring to make the whole solution homogeneous, while temperature rose to 75° C. 225 g of isopropyl bromide was slowly dropped into the obtained solution at 55±3° C. The resulting solution was continuously stirred further at 55±5° C. after the dropping was finished.

The reaction was terminated when 20 hours in total passed since the dropping started. A part of the reaction solution was taken as a sample and analyzed by high-performance liquid chromatography (HPLC). The result showed 67% of 4-isopropoxy-4'-hydroxydiphenyl sulfone, 32% of BPS and 1% of 4,4'-diisopropoxydiphenyl sulfone. The reaction solution was heated at 80° C. for an hour to evaporate unreacted isopropyl bromide to remove. Further, 24 ml of warm water (0.05 parts by weight to a part by weight of BPS) was added to the reaction solution and heated at 80° C. for an hour, and further 235 ml of warm water was added and heated at 80° C. for an hour to evaporate unreacted isopropyl bromide to remove. A part of the reaction solution was taken as a sample and analyzed by HPLC. The result showed 70% of 4-isopropoxy-4'-hydroxydiphenyl sulfone, 29% of BPS, and 1% of 4,4'-diisopropoxydiphenyl sulfone. An increase of a byproduct, 4,4'-diisopropoxydiphenyl sulfone, was not observed. Then, 300 ml of warm water and 250 ml of toluene were added to stir sufficiently and the aqueous layer was separated.

1100 ml of toluene and 200 ml of water were added to the aqueous layer at 79° C. and stirred at the same temperature for 30 minutes. Further, 30% dilute sulfuric acid was dropped little by little with stirring at 82° C. over an hour to adjust pH of the reaction solution uniformly to 8.4 to 8.7. The resulting solution was left to stand at 82° C. for 30 minutes and the toluene layer was separated.

300 ml of toluene and 300 ml of water were added to the toluene layer at 82° C., and 30% dilute sulfuric acid was dropped little by little with stirring at 82° C. over an hour to adjust pH of the whole solution uniformly to 8.3 to 8.6. The resulting solution was left to stand at 82° C. for 30 minutes and the toluene layer was separated. Further, 250 ml of toluene and 250 ml of water were added to the toluene layer at 82° C., and stirred at the same temperature for 2 hours. The resulting solution was left to stand at 82° C. for 30 minutes and the toluene layer was separated.

The toluene layer was cooled to 10 to 35° C. to deposit crystals. The crystals were separated by filtration, washed with water and dried to give 368.0 g of the target compound, 4-isopropoxy-4'-hydroxydiphenyl sulfone, as powder (yield: 70%). At this time, an amount of isopropyl bromide contained in the toluene layer was analyzed by gas chromatography, being 0.8% by weight.

The obtained powder of 4-isopropoxy-4'-hydroxydiphenyl sulfone was 99% or more in purity, and had a b value of 2.5 or less when measured by a color-difference meter (made by Nippon Denshoku Kogyo Co., Ltd, Model: 1001 DP). No coloring was observed.

COMPARATIVE EXAMPLE 3

Comparative Example Against Example 3

Example 2 was repeated to give 171.7 g of 4-isopropoxy-4'-hydroxydiphenyl sulfone as powder (yield: 70%), except that the process was omitted for removing unreacted isopropyl bromide by adding 300 ml of toluene to the reaction solution to heat at 80° C. for 3 hours after the reaction was completed.

The product was 99% or more in purity, and had a b value of 4.1 when measured by a color-difference meter (made by Nippon Denshoku Kogyo Co., Ltd, Model: 1001 DP). It was colored light yellow.

COMPARATIVE EXAMPLE 4

Comparative Example Against Example 4

450 g of BPS, 255 ml of a 48% aqueous solution of sodium hydroxide and 120 ml of water were placed in a reaction tank, and mixed with stirring to make the whole solution homogeneous, while temperature rose to 75° C. 225 g of isopropyl bromide was slowly dropped into the obtained solution at 55±3° C. The resulting solution was continuously stirred further at 55±5° C. after the dropping was finished.

The reaction was terminated when 20 hours in total passed since the dropping started. A part of the reaction solution was taken as a sample and analyzed by high-performance liquid chromatography (HPLC). The result showed 67% of 4-isopropoxy-4'-hydroxydiphenyl sulfone, 32% of BPS, and 1% of 4,4'-diisopropoxydiphenyl sulfone. 235 ml of warm water (0.52 parts by weight to a part by weight of BPS) was added to the reaction solution and heated at 80° C. for an hour to evaporate unreacted isopropyl bromide to remove. A part of the reaction solution was taken as a sample and analyzed by HPLC. The result showed 70% of 4-isopropoxy-4'-hydroxydiphenyl sulfone, 26% of BPS, and 4% of 4,4'-diisopropoxydiphenyl sulfone. An increase of a byproduct, 4,4'-diisopropoxydiphenyl sulfone, was observed. Then, 300 ml of warm water and 250 ml of toluene were added at 80° C. to stir sufficiently and the aqueous layer was separated.

1100 ml of toluene and 200 ml of water were added to the aqueous layer at 79° C. and stirred at the same temperature for 30 minutes. Further, 30% dilute sulfuric acid was dropped little by little with stirring at 82° C. over an hour to adjust pH of the reaction solution uniformly to 8.4 to 8.7. The resulting solution was left to stand at 82° C. for 30 minutes and the toluene layer was separated.

300 ml of toluene and 300 ml of water were added to the toluene layer at 82° C., and 30% dilute sulfuric acid was dropped little by little with stirring at 82° C. over an hour to adjust pH of the whole solution uniformly to 8.3 to 8.6. The resulting solution was left to stand at 82° C. for 30 minutes and the toluene layer was separated. Further, 250 ml of toluene and 250 ml of water were added to the toluene layer at 82° C., and stirred at the same temperature for 2 hours. The resulting solution was left to stand at 82° C. for 30 minutes and the toluene layer was separated.

The toluene layer was cooled to 10 to 35° C. to deposit crystals. The crystals were separated by filtration, washed with water and dried to give 368.0 g of the target compound, 4-isopropoxy-4'-hydroxydiphenyl sulfone, as powder (yield: 70%). At this time, an amount of isopropyl bromide contained in the toluene layer was analyzed by gas chromatography, being 0.8% by weight.

The obtained powder of 4-isopropoxy-4'-hydroxydiphenyl sulfone was 99% or more in purity, and had a b value of 2.5 or less when measured by a color-difference meter (made by Nippon Denshoku Kogyo Co., Ltd, Model: 1001 DP). No coloring was observed.

EXAMPLE 5

Example for (Composition 24) to (Composition 30)

In Example 5 and Reference Example 2, distilled water was used in all occasions. In Comparative Example 5 and Reference Example 3, industrial water was used throughout. The distilled water and industrial water were measured for the contents of iron components by an inductively coupled plasma-atomic emission spectroscope. The former contained 0.05 ppm or less of iron components and the latter 0.26 ppm.

GL tanks were used as reaction and purification tanks in Example 5 and Reference Example 2, and SUS tanks, which are usually used in the art, in Comparative Example 5 and Reference Example 3.

450 g of 4,4'-dihydroxydiphenyl sulfone (BPS), 255 ml of a 48% aqueous solution of sodium hydroxide and 120 ml of distilled water were placed in a GL tank, and mixed with stirring to make the whole solution homogeneous, while temperature rose to 75° C. 225 g of isopropyl bromide was slowly dropped into the obtained solution at 55±3° C. The resulting solution was continuously stirred further at 55±5° C. after the dropping was finished. When 20 hours in total passed since the dropping started, 235 ml of distilled water of 80° C. was added to the reaction solution. The resulting solution was heated at 80° C. for an hour to evaporate unreacted isopropyl bromide to remove. Then, 300 ml of distilled water of 80° C. and 250 ml of toluene were added at 80° C. to stir sufficiently and the aqueous layer was separated.

Then, 1100 ml of toluene and 200 ml of distilled water were added to the aqueous layer at 79° C. and stirred at the same temperature for 30 minutes. Further, 30% dilute sulfuric acid was dropped little by little with stirring at 82° C. over an hour to adjust pH of the reaction solution uniformly to 8.3 to 8.7. The resulting solution was left to stand at 82° C. for 30 minutes and the toluene layer was separated. Further, 250 ml of toluene and 250 ml of water were added to the toluene layer at 82° C., and stirred at the same temperature for 2 hours. The resulting solution was left to stand at 82° C. for 30 minutes and the toluene layer was separated.

The obtained toluene layer was cooled to deposit crystals. The crystals were separated by filtration, washed with water and dried to give 368.0 g of the target compound, 4-isopropoxy-4'-hydroxydiphenyl sulfone, as powder (yield: 70%).

The obtained 4-isopropoxy-4'-hydroxydiphenyl sulfone was 98% or more in purity, and had a b value of 2.5 or less when measured by a color-difference meter (made by Nippon Denshoku Kogyo Co., Ltd, Model: 1001 DP). No coloring was observed.

COMPARATIVE EXAMPLE 5

Comparative Example Against Example 5

Example 4 was repeated to give 368.0 g of 4-isopropoxy-4'-hydroxydiphenyl sulfone as powder (yield: 70%), except that SUS tanks were used instead of the GL tanks and industrial water instead of distilled water.

The obtained 4-isopropoxy-4'-hydroxydiphenyl sulfone was 98% or more in purity, and had a b value of 4.1 when measured by a color-difference meter (made by Nippon Denshoku Kogyo Co., Ltd, Model: 1001 DP). It was colored light pink.

REFERENCE EXAMPLE 2

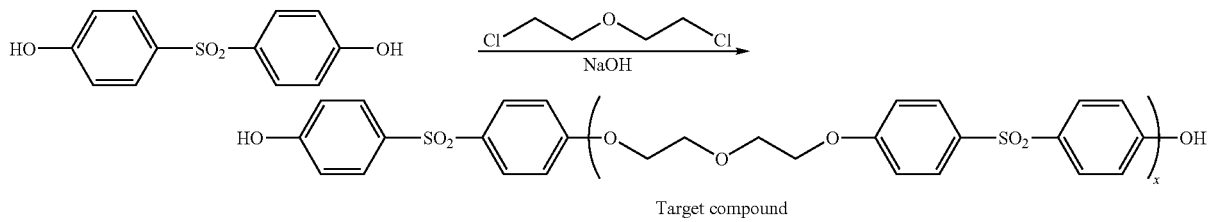

Target compound (Wherein, x is an integer of 1 to 10).

47.5 ml of distilled water, 25.6 g of sodium hydroxide and 80.0 g of 4,4'-dihydroxydiphenyl sulfone were placed in a GL tank, and stirred to dissolve at 110±2° C. for 4 hours. To the resulting solution was added 20.34 g of bis(2-chloroethyl) ether at 110 to 112° C. and stirred at the same temperature for 8 hours. After the reaction was completed, 108.1 ml of hot water was added to the reaction solution and cooled to 80° C. 167.4 ml of a 90% aqueous methanol solution was added at 70° C. and stirred for 30 minutes to make the solution homogeneous. Then, 116.4 g of 10% hydrochloric acid was slowly dropped at 71° C. to make pH 4 to 5. The resulting solution was left at 71° C. for an hour, cooled to 25 to 30° C., and further left for 8 hours. The deposited crystals were separated by filtration, washed with 200 ml of a 50% aqueous methanol solution and dried to give 63.2 g of the target compound as powder. Yield: 78%.

The obtained target compound was 99% or more in purity, and had a b value of 2.5 or less when measured by a color-difference meter (made by Nippon Denshoku Kogyo Co., Ltd, Model: 1001 DP). No coloring was observed.

REFERENCE EXAMPLE 3

Reference Example 2 was repeated to give 63.2 g of the target compound as powder (yield: 78%), except that SUS tanks were used instead of the GL tanks and industrial water instead of distilled water.

The obtained target compound was 98% or more in purity, and had a b value of 4.1 when measured by a color-difference meter (made by Nippon Denshoku Kogyo Co., Ltd, Model: 1001 DP). It was colored light pink.

EXAMPLE 6

Example for (Composition 31)

Water used in Examples 6 and 7, Comparative Example 6 and Reference Examples 4 and 5 was industrial water of general use. A measurement by an inductively coupled plasma-atomic emission spectroscope showed that the content of metal ions in the industrial water was 0.1 ppm or more.

450 g of 4,4'-dihydroxydiphenyl sulfone (BPS), 255 ml of a 48% aqueous solution of sodium hydroxide and 120 ml of water were placed in an SUS reaction tank, and mixed with stirring to make the whole solution homogeneous, while temperature rose to 75° C. 225 g of isopropyl bromide was slowly dropped into the obtained solution at 55±3° C. The resulting solution was continuously stirred further at 55±5° C. after the dropping was finished. 235 ml of warm water was added to the reaction solution when 20 hours in total passed since the dropping started. The resulting solution was heated at 80° C. for an hour to evaporate unreacted isopropyl bromide to remove. Then, 300 ml of warm water and 250 ml of toluene were added at 80° C. to stir sufficiently and the aqueous layer was separated.

Then, 1100 ml of toluene and 200 ml of water were added to the aqueous layer at 79° C. and stirred at the same temperature for 30 minutes. Further, 30% dilute sulfuric acid was dropped little by little with stirring at 82° C. over an hour to adjust pH of the reaction solution uniformly to 8.3 to 8.7, and 2.7 ml of a 5% aqueous solution of EDTA disodium salt was added. The resulting solution was left to stand at 82° C. for 30 minutes and the toluene layer was separated. Further, 250 ml of toluene and 250 ml of water were added to the toluene layer at 82° C., and stirred at the same temperature for 2 hours. The resulting solution was left to stand at 82° C. for 30 minutes and the toluene layer was separated.

The toluene layer was cooled to deposit crystals. The crystals were separated by filtration, washed with water and dried to give 368.0 g of the target compound, 4-isopropoxy-4'-hydroxydiphenyl sulfone, as powder (yield: 70%).

The obtained 4-isopropoxy-4'-hydroxydiphenyl sulfone was 98% or more in purity, and had a b value of 2.5 or less when measured by a color-difference meter (made by Nippon Denshoku Kogyo Co., Ltd, Model: 1001 DP). No coloring was observed.

EXAMPLE 7

Example for (Composition 31)

210 g of 4,4'-dihydroxydiphenyl sulfone (BPS), 74.2 ml of a 48% aqueous solution of sodium hydroxide and 740 ml of water were placed in an SUS reaction tank, and mixed with stirring to make the whole solution homogeneous, while temperature rose to 80° C. To the obtained solution was added 705 ml of toluene at 70° C., and 165 g of isopropyl bromide (iPr—Br) was slowly dropped. The resulting solution was stirred at 76 to 80° C. for 8 hours. Then, 4.8 ml of a 48% aqueous solution of sodium hydroxide and 22 g of isopropyl bromide were added and stirred at 78 to 80° C. for 6 hours. Further, 3.3 ml of a 48% aqueous solution of sodium hydroxide and 25 g of isopropyl bromide were added and reacted at 78 to 81° C. for 8 hours. After the reaction was completed, 300 ml of toluene was added to the reaction solution, and heated at 80° C. for 3 hours to evaporate unreacted isopropyl bromide to remove completely.

Then, 200 ml of water, 694 ml of toluene, 2.5 g of anhydrous sodium carbonate (soda ash) and 10 ml of warm water were added and further a 48% aqueous solution of sodium hydroxide was added to adjust pH of the reaction solution to 8.55±0.02. To the resulting solution was added 1.2 ml of a 5% aqueous solution of EDTA disodium salt and left to stand for 30 minutes. The toluene layer was then separated. 500 ml of water and 800 ml of toluene were added to the toluene layer at 75 to 80° C., and stirred at the same temperature for 30 minutes. The toluene layer was separated.

The toluene layer was cooled. The deposited crystals were separated by filtration, washed with water and dried to give 171.7 g of the target compound, 4-isopropoxy-4'-hydroxydiphenyl sulfone, as powder (yield: 70%).

The obtained 4-isopropoxy-4'-hydroxydiphenyl sulfone was 98% or more in purity, and had a b value of 2.5 or less when measured by a color-difference meter (made by Nippon Denshoku Kogyo Co., Ltd, Model: 1001 DP). No coloring was observed.

COMPARATIVE EXAMPLE 6

Comparative Example Against Example 5

Example 5 was repeated to give 368.0 g of 4-isopropoxy-4'-hydroxydiphenyl sulfone as powder (yield: 70%), except that the operation of adding a 5% aqueous solution of EDTA disodium salt to the reaction solution was omitted in the purification process.

The obtained 4-isopropoxy-4'-hydroxydiphenyl sulfone was 98% or more in purity, and had a b value of 4.1 when measured by a color-difference meter (made by Nippon Denshoku Kogyo Co., Ltd, Model: 1001 DP). It was colored light yellow.

REFERENCE EXAMPLE 4

Production of the Same Target Compound as that in Reference Example 2

In a 500-ml, four-neck flask were placed 47.5 ml of water, 25.6 g of sodium hydroxide and 80.0 g of 4,4'-dihydroxydiphenyl sulfone and stirred to dissolve at 110±2° C. for 4 hours. 20.34 g of bis(2-chloroethyl) ether was added to the resulting solution at 110 to 112° C., and stirred at the same temperature for 8 hours. After the reaction was completed, 108.1 ml of hot water was added to the reaction solution and cooled to 80° C. 167.4 ml of a 90% aqueous methanol solution was added to the resulting solution and stirred for 30 minutes to make the solution homogeneous. Then, 0.5 ml of a 5% aqueous solution of EDTA disodium salt was added and 116.4 g of 10% hydrochloric acid was slowly dropped at 71° C. to adjust pH to 4 to 5. The resulting solution was left at 71° C. for an hour, cooled to 25 to 30° C., and further left for 8 hours. The deposited crystals were separated by filtration, washed with 200 ml of a 50% aqueous methanol solution, and dried to give 63.2 g of the target compound as powder. Yield: 78%.

The target compound was 99% or more in purity, and had a b value of 2.5 or less when measured by a color-difference meter (made by Nippon Denshoku Kogyo Co., Ltd, Model: 1001 DP). No coloring was observed.

REFERENCE EXAMPLE 5

Reference Example 4 was repeated to give 63.2 g of the target compound as powder (yield: 78%), except that the operation of adding a 5% aqueous solution of EDTA disodium salt to the reaction solution was omitted in the purification process.

The obtained target compound was 98% or more in purity, and had a b value of 4.1 when measured by a color-difference meter (made by Nippon Denshoku Kogyo Co., Ltd, Model: 1001 DP). It was colored light yellow.

EXAMPLE 7

Example for (Composition 32) to (Composition 37)

577 g of 4-isopropoxy-4'-hydroxydiphenyl sulfone, that was crystallized from toluene and filtrated in the same way as those in Reference Example 1 and Example 1 and not dried yet, formed a molecular compound with toluene, and had the toluene solvent attached in addition to the salvation toluene. The 4-isopropoxy-4'-hydroxydiphenyl sulfone before being dried was heated to dry under reduced pressure with a paddle dryer under the following operation conditions:

Pressure reduction degree: 60 to 150 mmHg
Heating temperature: 80 to 85° C.
Stirring rate: 2 to 3 revolutions/minute
Drying duration: 16 hours After the compound was dried, 4-isopropoxy-4'-hydroxydiphenyl sulfone contained 0.1% by weight or less of toluene. No block particles were observed. The product was easily pulverized to fine particles even in the subsequent pulverization process.

COMPARATIVE EXAMPLE 7

Comparative Example Against Example 7

4-Isopropoxy-4'-hydroxydiphenyl sulfone of the same conditions as those in Example 7 was heated to dry under the same conditions as those in Example 8, except that a dryer with heating under reduced pressure without a stirring apparatus was used, instead of a paddle dryer. After the compound was dried, there were a large amount of block particles observed. The compound after dried was heavier than that in Example 7. Besides, it took a long time to pulverize the compound to a particle size preset for the product in the subsequent pulverization process.

Applicability in Industry

As described above, the present invention relates to methods for producing 4,4'-dihydroxydiphenyl sulfone monoethers, in which a non-colored, highly pure target compound can be efficiently isolated from a mixture that even contains the target compound and impurities at high concentrations.

4,4'-Dihydroxydiphenyl sulfone monoethers are compounds useful as developers. The methods of the present invention stably provide products of high quality, having a high value of use in industry.

What is claimed:

1. A process for the preparation of a non-colored compound of Formula (I), which has a b value of 2.5 or less when measured by a color difference meter,

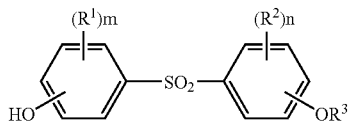

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

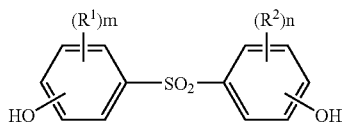

wherein R¹, R², m and n are as defined above
with a compound of Formula (III)

$$R^3-X \quad\quad (III)$$

wherein R³ is as defined above and X is a halogen
in a solvent in the presence of a base;
extracting the compound of Formula (I) at a pH of between about 8.0 and about 9.0 with an organic solvent, wherein the concentration of the compound of Formula (III) in the organic solvent is 5% by weight or less; and
purifying by adding water or pH adjusted water to achieve a pH of between about 8.3 and about 8.6;
wherein the compound of Formula (I) is obtained in an amount of at least about 63 grams.

2. A process for the preparation of a non-colored compound of Formula (I), which has a b value of 2.5 or less when measured by a color difference meter,

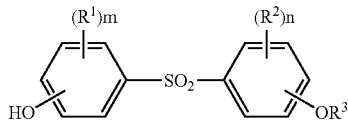

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

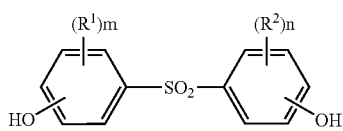

wherein R¹, R², m and n are as defined above
with an excess amount of a compound of Formula (III)

$$R^3-X \quad\quad (III)$$

wherein R³ is as defined above and X is a halogen
in a solvent in the presence of a base to form a reaction solution;
purifying the obtained reaction solution by removing the unreacted portion of the compound of Formula (III) with the solvent from the reaction solution by distillation after the compounds of Formula (II) and (III) are reacted and before diether as a byproduct is extracted; and
crystallizing the compound of Formula (I) from an organic solvent of the reaction solution or a solution obtained in the purification of the compound of Formula (I) from the reaction solution, wherein the concentration of the compound of Formula (III) in the organic solvent is 1% by weight or less;
wherein the compound of Formula (I) is obtained in an amount of at least about 63 grams.

3. The process according to claim 2, wherein the reaction of compounds of Formula (II) and (III) is completed prior to removing the compound of Formula (III).

4. The process according to claim 2 further comprising adjusting the pH of the reaction solution to about 8.0 to 9.0 immediately after removing the compound of Formula (III).

5. The process according to claim 2, comprising removing the compound of Formula (III) and a mixture of water and a solvent azeotropic with water by distillation.

6. The process according to claim 2, wherein the solvent is water.

7. A process for the preparation of a non-colored compound of Formula (I), which has a b value of 2.5 or less when measured by a color difference meter,

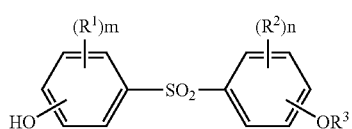

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

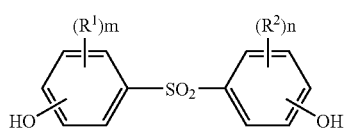

wherein R¹, R², m and n are as defined above
with an excess amount of a compound of Formula (III)

$$R^3-X \quad\quad (III)$$

wherein R³ is as defined above and X is a halogen
in a solvent in the presence of a base to form a reaction solution; and purifying the reaction solution by extraction in water and an organic solvent such that the concentration of the compound of Formula (III) in the organic solvent is 5% by weight or less;
wherein the compound of Formula (I) is obtained in an amount of at least about 63 grams.

8. The process according to claim 7, wherein the concentration of the compound of Formula (III) in the organic solvent is 2% by weight or less.

9. The process according to claim 7, wherein the concentration of the compound of Formula (III) in the organic solvent is 1% by weight or less.

10. A process for the preparation of a non-colored compound of Formula (I), which has a b value of 2.5 or less when measured by a color difference meter,

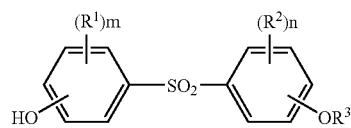

(I)

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising reacting a compound of Formula (II)

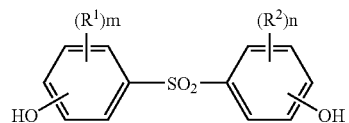

(II)

wherein $R^1$, $R^2$, m and n are as defined above
with an excess amount of a compound of Formula (III)

$R^3$—X    (III)

wherein $R^3$ is as defined above and X is a halogen
in the presence of 1.5 to 3 moles of an alkali to one mole of the compound of Formula (II) in 0.3 to 1.5 parts by weight of an aqueous solvent to one part by weight of the compound of Formula (II) to form a reaction solution;
distilling the reaction solution to remove the compound of Formula (III) followed by adding an amount of water to the distilled reaction solution to further remove the compound of Formula (III); and
crystallizing the compound of Formula (I) from an organic solvent, wherein the concentration of the compound of Formula (III) in the organic solvent is 1% by weight or less:
wherein the compound of Formula (I) is obtained in an amount of at least about 63 grams.

11. The process according to claim 10, wherein the amount of water added is in the range of 0.03 to 0.1 parts by weight to one part by weight of the compound of Formula (II).

12. The process according to claim 10, wherein the amount of water added is in the range of 0.04 and 0.08 parts by weight to one part by weight of the compound of Formula (II).

13. The process according to claim 10, wherein the amount of water is added in two or more additions.

14. The process according to claim 13, wherein the amount of water added in a first addition is in the range of 0.03 and 0.1 parts by weight to one part by weight of the compound of Formula (II).

15. The process according to claim 13, wherein the amount of water added is between 0.04 and 0.08 parts by weight to one part by weight of the compound of Formula (II).

16. A process for the preparation of a non-colored compound of Formula (I), which has a b value of 2.5 or less when measured by a color difference meter,

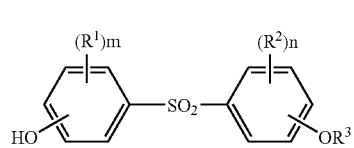

(I)

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising
producing a solvent having 0.05 ppm or less of iron components and
reacting in the solvent in the presence of a base, a compound of Formula (II)

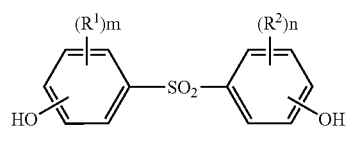

(II)

wherein $R^1$, $R^2$, m and n are as defined above
with a compound of Formula (III)

$R^3$—X    (III)

wherein $R^3$ is as defined above and X is a halogen,
wherein the compound of Formula (I) is obtained in an amount of at least about 63 grams.

17. The process according to claim 16, wherein the reaction solvent is a reaction solvent comprising water.

18. A process for the preparation of a non-colored compound of Formula (I), which has a b value of 2.5 or less when measured by a color difference meter,

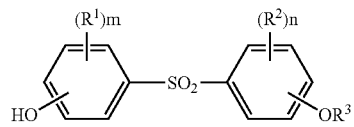

(I)

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising
producing water having 0.05 ppm or less of iron components,
reacting a compound of Formula (II)

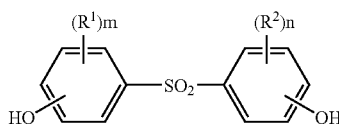

wherein R¹, R², m and n are as defined above
with a compound of Formula (III)

R³—X    (III)

wherein R³ is as defined above and X is a halogen
in a solvent in the presence of a base, and
purifying by adding the water,
wherein the compound of Formula (I) is obtained in an amount of at least about 63 grams.

19. A process for the preparation of a non-colored compound of Formula (I), which has a b value of 2.5 or less when measured by a color difference meter,

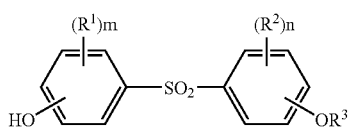

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

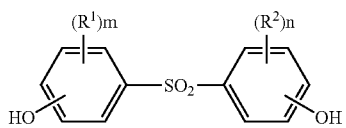

wherein R¹, R², m and n are as defined above
with a compound of Formula (III)

R³—X    (III)

wherein R³ is as defined above and X is a halogen
in a solvent in the presence of a base
in a tank with a corrosion-resistant layer over the inner wall, in which the corrosion-resistant layer comprises at least one corrosion-resistant material selected from the group consisting of titanium, zirconium, tantalum, niobium and nickel, borosilicate glass, neutral glass, quartz glass and alkali-resistant glass, enamel, ethylene tetrafluoride resins (PTFE or TFE), ethylene tetrafluoride-perfluoroalkoxy vinyl ether copolymers (PFA), ethylene tetrafluoride-propylene hexafluoride copolymers (FEP), polychlorotrifluoroethylene (PCTFE), ethylene tetrafluoride-ethylene copolymers (ETFE), chlorotrifluoroethylene-ethylene copolymers (ECTFE), polyvinylidene fluoride (PVDF) and polyvinyl fluoride (PVF),
wherein the compound of Formula (I) is obtained in an amount of at least about 63 grams.

20. A process for the preparation of a non-colored compound of Formula (I), which has a b value of 2.5 or less when measured by a color difference meter,

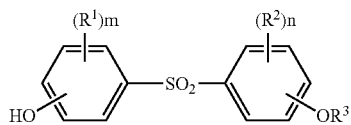

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

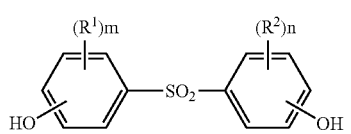

wherein R¹, R², m and n are as defined above
with a compound of Formula (III)

R³—X    (III)

wherein R³ is as defined above and X is a halogen
in a solvent in the presence of a base, and
purifying the reaction solution in a tank with a corrosion-resistant layer over the inner wall, in which the corrosion-resistant layer comprises at least one corrosion-resistant material selected from the group consisting of titanium, zirconium, tantalum, niobium and nickel, borosilicate glass, neutral glass, quartz glass and alkali-resistant glass, enamel, ethylene tetrafluoride resins (PTFE or TFE), ethylene tetrafluoride-perfluoroalkoxy vinyl ether copolymers (PFA), ethylene tetrafluoride-propylene hexafluoride copolymers (FEP), polychlorotrifluoroethylene (PCTFE), ethylene tetrafluoride-ethylene copolymers (ETFE), chlorotrifluoroethylene-ethylene copolymers (ECTFE), polyvinylidene fluoride (PVDF) and polyvinyl fluoride (PVF),
wherein the compound of Formula (I) is obtained in an amount of at least about 63 grams.

21. A process for the preparation of a non-colored compound of Formula (I), which has a b value of 2.5 or less when measured by a color difference meter,

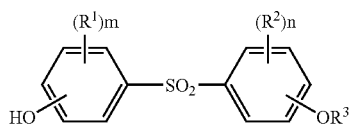

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising reacting a compound of Formula (II)

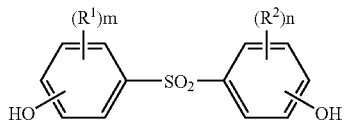
(II)

wherein R¹, R², m and n are as defined above with a compound of Formula (III)

R³—X (III)

wherein R³ is as defined above and X is a halogen in a solvent in the presence of a base, and purifying by adding a chelating agent, wherein the compound of Formula (I) is obtained in an amount of at least about 63 grams.

22. A process for the preparation of a non-colored compound of 4-isopropoxy-4'-hydroxydiphenyl sulfone, which has a b value of 2.5 or less when measured by a color difference meter and is not block particles, comprising crystallizing the compound of 4-isopropoxy-4'-hydroxydiphenyl sulfone from an organic solvent, wherein the concentration of an alkyl halide in the organic solvent is 1% by weight or less, and purifying by drying with mechanical stirring, wherein the compound of 4-isopropoxy-4'-hydroxydiphenyl sulfone is obtained in an amount of at least about 63 grams.

23. The process according to claim 22, wherein the product is heated under reduced pressure with mechanical stirring.

24. The process according to claim 22, wherein the melting temperature of the compound of 4-isopropoxy-4'-hydroxydiphenyl sulfone before being dried is lower than the melting temperature of the compound of 4-isopropoxy-4'-hydroxydiphenyl sulfone.

25. The process according to claim 22, wherein the compound of 4-isopropoxy-4'-hydroxydiphenyl sulfone before being dried has formed a molecular compound with a solvent.

26. The process according to claim 25, wherein the solvent is an organic solvent.

27. The process according to claim 26, wherein the organic solvent is an aromatic hydrocarbon.

28. The process according to claim 2, wherein the compound of Formula (I) is a compound represented by Formula (IV)

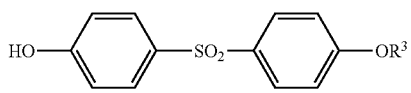
(IV)

wherein R³ is an alkyl having 1 to 8 carbons, an alkenyl having 2 to 8 carbons, a cycloalkyl having 3 to 8 carbons or an optionally substituted aralkyl.

29. The process according to claim 7, wherein the compound of Formula (I) is a compound represented by Formula (IV)

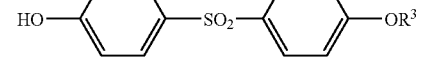
(IV)

wherein R³ is an alkyl having 1 to 8 carbons, an alkenyl having 2 to 8 carbons, a cycloalkyl having 3 to 8 carbons or an optionally substituted aralkyl.

30. The process according to claim 10, wherein the compound of Formula (I) is a compound represented by Formula (IV)

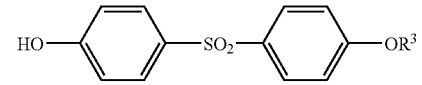
(IV)

wherein R³ is an alkyl having 1 to 8 carbons, an alkenyl having 2 to 8 carbons, a cycloalkyl having 3 to 8 carbons or an optionally substituted aralkyl.

31. The process according to claim 16, wherein the compound of Formula (I) is a compound represented by Formula (IV)

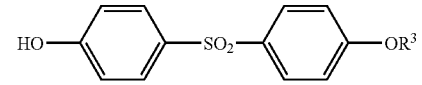
(IV)

wherein R³ is an alkyl having 1 to 8 carbons, an alkenyl having 2 to 8 carbons, a cycloalkyl having 3 to 8 carbons or an optionally substituted aralkyl.

32. The process according to claim 18, wherein the compound of Formula (I) is a compound represented by Formula (IV)

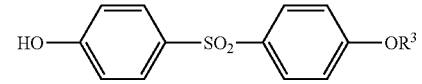
(IV)

wherein R³ is an alkyl having 1 to 8 carbons, an alkenyl having 2 to 8 carbons, a cycloalkyl having 3 to 8 carbons or an optionally substituted aralkyl.

33. The process according to claim 19, wherein the compound of Formula (I) is a compound represented by Formula (IV)

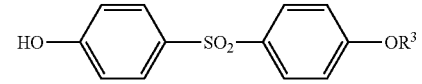
(IV)

wherein R³ is an alkyl having 1 to 8 carbons, an alkenyl having 2 to 8 carbons, a cycloalkyl having 3 to 8 carbons or an optionally substituted aralkyl.

34. The process according to claim 20, wherein the compound of Formula (I) is a compound represented by Formula (IV)

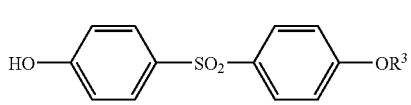

wherein R³ is an alkyl having 1 to 8 carbons, an alkenyl having 2 to 8 carbons, a cycloalkyl having 3 to 8 carbons or an optionally substituted aralkyl.

35. The process according to claim 21, wherein the compound of Formula (I) is a compound represented by Formula (IV)

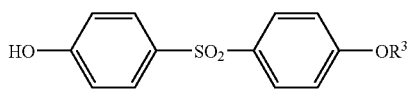

wherein R³ is an alkyl having 1 to 8 carbons, an alkenyl having 2 to 8 carbons, a cycloalkyl having 3 to 8 carbons or an optionally substituted aralkyl.

36. A process for the preparation of a non-colored compound of Formula (IV), which has a b value of 2.5 or less when measured by a color difference meter and is not block particles,

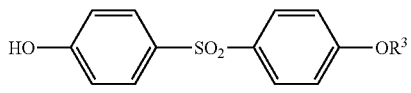

wherein R³ is an alkyl having 1 to 8 carbons, an alkenyl having 2 to 8 carbons, a cycloalkyl having 3 to 8 carbons or an optionally substituted aralkyl, comprising crystallizing the compound of Formula (IV) from an organic solvent, wherein the concentration of an alkyl halide in the organic solvent is 1% by weight or less, and purifying by drying with mechanical stirring, wherein the compound of Formula (IV) is obtained in an amount of at least about 63 grams.

37. A process for the preparation of a non-colored compound of Formula (I), which has a b value of 2.5 or less when measured by a color difference meter,

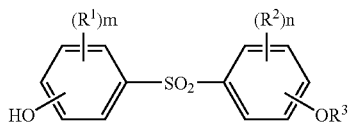

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising the steps of:

reacting a compound of Formula (II)

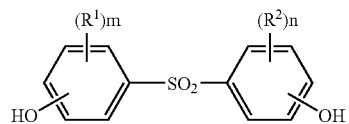

wherein R¹, R², m and n are as defined above
with an excess amount of a compound of Formula (III)

R³—X  (III)

wherein R³ is as defined above and X is a halogen
in a solvent in the presence of a base to form a reaction solution;

purifying the obtained reaction solution by removing the unreacted portion of the compound of Formula (III) with the solvent from the reaction solution by distillation after the compounds of Formula (II) and (III) are reacted and before diether as a byproduct is extracted;

extracting diether as a byproduct; and crystallizing the compound of Formula (I) from an organic solvent, wherein the concentration of the compound of Formula (III) in the organic solvent is 1% by weight or less;

wherein the compound of Formula (I) is obtained in an amount of at least about 63 grams.

38. A process for the preparation of a non-colored compound of Formula (I), which has a b value of 2.5 or less when measured by a color difference meter.

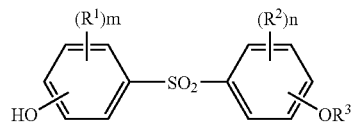

wherein R¹ and R² are each independently a halogen, an alkyl having 1 to 8 carbons or an alkenyl having 2 to 8 carbons; m and n are each independently 0 or an integer of 1 to 4; and R³ is an alkyl having 1 to 8 carbons, an alkenyl having 2 to 8 carbons, a cycloalkyl having 3 to 8 carbons or an optionally substituted aralkyl, comprising the step of reacting a compound of Formula (II)

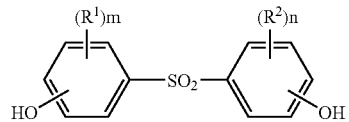

wherein R¹, R², m and n are as defined above
with an excess amount of a compound of Formula (III)

R³—X  (III)

wherein R³ is as defined above and X is a halogen
in a solvent comprising 0.05 ppm or less of iron components, wherein the compound of Formula (I) is obtained in an amount of at least about 63 grams.

39. A process for the preparation of a non-colored compound of Formula (I), which has a b value of 2.5 or less when measured by a color difference meter,

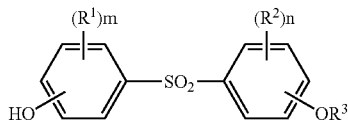

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising the steps of:

reacting a compound of Formula (II)

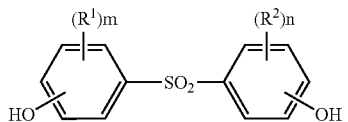

wherein $R^1$, $R^2$, m and n are as defined above
with an excess amount of a compound of Formula (III)

$$R^3—X \qquad (III)$$

wherein $R^3$ is as defined above and X is a halogen; and
purifying by adding water comprising 0.05 ppm or less of iron components;
wherein the compound of Formula (I) is obtained in an amount of at least about 63 grams.

40. A process for the preparation of a non-colored compound of Formula (I), which has a b value of 2.5 or less when measured by a color difference meter,

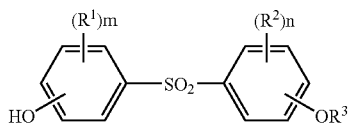

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising the step of
reacting a compound of Formula (II)

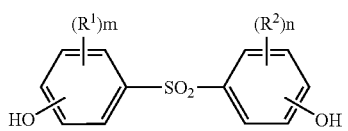

wherein $R^1$, $R^2$, m and n are as defined above
with an excess amount of a compound of Formula (III)

$$R^3—X \qquad (III)$$

wherein $R^3$ is as defined above and X is a halogen
in a tank with a corrosion-resistant layer over the inner wall,
wherein the compound of Formula (I) is obtained in an amount of at least about 63 grams.

41. A process for the preparation of a non-colored compound of Formula (I), which has a b value of 2.5 or less when measured by a color difference meter,

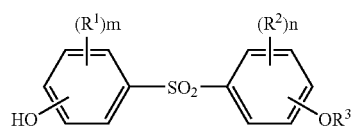

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising the steps of:
reacting a compound of Formula (II)

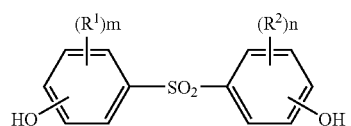

wherein $R^1$, $R^2$, m and n are as defined above
with an excess amount of a compound of Formula (III)

$$R^3—X \qquad (III)$$

wherein $R^3$ is as defined above and X is a halogen; and
purifying the reaction solution in a tank with a corrosion-resistant layer over the inner wall;
wherein the compound of Formula (I) is obtained in an amount of at least about 63 grams.

42. A process for the preparation of a non-colored compound of Formula (I), which has a b value of 2.5 or less when measured by a color difference meter,

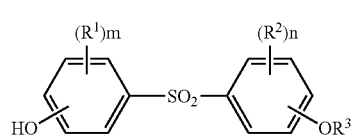

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising the steps of:
reacting a compound of Formula (II)

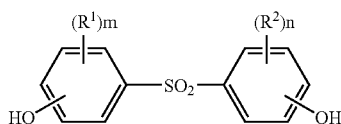

(II)

wherein $R^1$, $R^2$, m and n are as defined above
with an excess amount of a compound of Formula (III)

$$R^3—X \quad (III)$$

wherein $R^3$ is as defined above and X is a halogen; and
purifying by adding a chelating agent;
wherein the compound of Formula (I) is obtained in an amount of at least about 63 grams.

43. A process for the preparation of a non-colored compound of Formula (I), which has a b value of 2.5 or less when measured by a color difference meter,

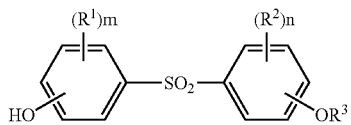

(I)

wherein $R^1$ and $R^2$ are each independently a halogen, an alkyl having 1 to 8 carbons or an alkenyl having 2 to 8 carbons; m and n are each independently 0 or an integer of 1 to 4; and $R^3$ is an alkyl having 1 to 8 carbons, an alkenyl having 2 to 8 carbons, a cycloalkyl having 3 to 8 carbons or an optionally substituted aralkyl, comprising the steps of:

reacting a compound of Formula (II)

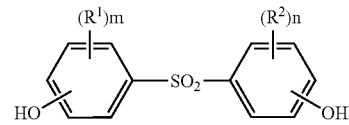

(II)

wherein $R^1$, $R^2$, m and n are as defined above
with an excess amount of a compound of Formula (III)

$$R^3—X \quad (III)$$

wherein $R^3$ is as defined above and X is a halogen;
crystallizing the compound of Formula (I) from an organic solvent, wherein the concentration of the compound of Formula (III) in the organic solvent is 1% by weight or less, and
purifying by drying with mechanical stirring;
wherein the compound of Formula (I) is obtained in an amount of at least about 63 grams.

44. The process according to claim 21, wherein the chelating agent is at least one material selected from the group consisting of: compounds obtained from reactions of compounds having amino groups, such as ammonia, polyamine and amino acids, with carbon disulfide, halogenated carboxylic acids, halogenated alcohols and the like; salts of these compounds; dithiocarbamates; dimethylglyoxime; dithizone; bipyridine; and phenanthroline.

* * * * *